(12) United States Patent
Shinzato et al.

(10) Patent No.: US 11,467,170 B2
(45) Date of Patent: Oct. 11, 2022

(54) DOSE DETERMINATION PROGRAM AND DOSE DETERMINATION DEVICE

(71) Applicant: NIPRO CORPORATION, Osaka (JP)

(72) Inventors: Toru Shinzato, Toyohashi (JP); Wataru Mizuno, Osaka (JP); Hidetoshi Saio, Osaka (JP)

(73) Assignee: NIPRO CORPORATION, Osaka (JP)

( * ) Notice: Subject to any disclaimer, the term of this patent is extended or adjusted under 35 U.S.C. 154(b) by 262 days.

(21) Appl. No.: 16/622,373

(22) PCT Filed: Jul. 17, 2018

(86) PCT No.: PCT/IB2018/055267
§ 371 (c)(1),
(2) Date: Dec. 13, 2019

(87) PCT Pub. No.: WO2018/229739
PCT Pub. Date: Dec. 20, 2018

(65) Prior Publication Data
US 2020/0200770 A1 Jun. 25, 2020

(30) Foreign Application Priority Data

Jun. 14, 2017 (JP) .............................. JP2017-116692
Jul. 28, 2017 (JP) .............................. JP2017-146807

(51) Int. Cl.
*G01N 33/72* (2006.01)
*G01N 33/48* (2006.01)

(52) U.S. Cl.
CPC ........... *G01N 33/726* (2013.01); *G01N 33/48* (2013.01); *G01N 33/721* (2013.01)

(58) Field of Classification Search
CPC ........... A61K 38/22; A61P 13/12; A61P 7/06; G01N 33/48; G01N 33/72; G01N 33/721; G01N 33/726; C07K 14/505
USPC ................................ 436/63, 66; 422/68.1, 73
See application file for complete search history.

(56) References Cited

U.S. PATENT DOCUMENTS

| | | | |
|---|---|---|---|
| 6,747,002 | B2 | 6/2004 | Cheung et al. |
| 2003/0198691 | A1 | 10/2003 | Cheung et al. |
| 2004/0157778 | A1 | 8/2004 | Cheung et al. |
| 2004/0176297 | A1 | 9/2004 | Cheung et al. |
| 2006/0100150 | A1 | 5/2006 | Cheung et al. |
| 2006/0128624 | A1 | 6/2006 | Cheung et al. |
| 2013/0052136 | A1 | 2/2013 | Chamney et al. |
| 2013/0085772 | A1 | 4/2013 | Gaweda et al. |
| 2013/0191097 | A1 | 7/2013 | Hocum et al. |
| 2014/0128791 | A1 | 5/2014 | Fuertinger et al. |
| 2014/0157778 | A1 | 6/2014 | Ponnuraj et al. |
| 2014/0200054 | A1 | 7/2014 | Fraden |
| 2014/0200181 | A1* | 7/2014 | Fuertinger ............. G16H 50/50 514/7.7 |
| 2015/0220700 | A1 | 8/2015 | Chait et al. |
| 2016/0085939 | A1 | 3/2016 | Shinzato et al. |
| 2017/0128532 | A1* | 5/2017 | Rodriguez ......... G01N 33/5044 |
| 2018/0092892 | A1 | 4/2018 | Smith et al. |
| 2018/0218110 | A1 | 8/2018 | Hocum et al. |
| 2018/0284140 | A1 | 10/2018 | Chamney et al. |
| 2021/0012872 | A1* | 1/2021 | Gaweda ................. A61B 34/10 |
| 2021/0313024 | A1* | 10/2021 | Fujikawa ............... G16H 50/20 |

FOREIGN PATENT DOCUMENTS

| | | |
|---|---|---|
| EP | 2416154 A1 | 2/2012 |
| EP | 3009843 A1 | 4/2016 |
| JP | 2005-247858 A | 9/2005 |
| JP | 2013-516680 A | 5/2013 |
| JP | 2013-527430 A | 6/2013 |
| JP | 2015-000109 A | 1/2015 |
| JP | 2015000109 A | 1/2015 |
| JP | 2016029525 A | 3/2016 |
| WO | 2011082421 A1 | 7/2011 |
| WO | 2014/200054 A1 | 12/2014 |
| WO | 2016/161094 A1 | 10/2016 |

OTHER PUBLICATIONS

Dana C. Miskulin, MD, MS, et al., "Computerized Decision Support for EPO Dosing in Hemodialysis Patients", American Journal of Kidney Diseases, Dec. 2009, pp. 1081-1088, vol. 54, No. 6.
Hirokatsu Atsumi, et al., "Computerized Decision Support (CDS) for Dosing of Iron and Erythropoiesis-stimulating Agents in Hemodialysis Patients", J. Kanazawa Medical University, Dec. 2011, pp. 119-123, vol. 36, No. 4.
Steven Fishbane, et al., "Hemoglobin cycling in hemodialysis patients treated with recombinant human erythropoietin", Kidney International, 2005, pp. 1337-1343, vol. 68.
International Search Report for PCT/IB2018/055267 dated Oct. 9, 2018 [PCT/ISA/210].
Communication dated Feb. 11, 2021, from the European Patent Office in European Application No. 18818916.1.
Adam E. Gaweda et al., "Using clinical information in goal-oriented learning", IEEE Engineering in Medicine and Biology Magazine, vol. 26, No. 2, Mar. 2007, pp. 27-36.

\* cited by examiner

Primary Examiner — Maureen Wallenhorst
(74) Attorney, Agent, or Firm — Sughrue Mion, PLLC

(57) ABSTRACT

A dose determination program for an erythropoiesis-stimulating agent that is executable by a computer. The program causes the computer to perform: obtaining a predetermined target hemoglobin concentration; obtaining a first concentration and a first dose in a stable state in which a hemoglobin concentration is stable at the first concentration by repeatedly administering the first dose a plurality of times, and calculating a second dose of the erythropoiesis-stimulating agent based on the obtained target hemoglobin concentration, the obtained first concentration, and the obtained first dose, the second dose of the erythropoiesis-stimulating agent being to be administered by a fixed amount.

12 Claims, 12 Drawing Sheets

DOSE DETERMINATION PROGRAM AND DOSE DETERMINATION DEVICE

CROSS REFERENCE TO RELATED APPLICATIONS

This application is a National Stage of International Application No. PCT/IB2018/055267 filed Jul. 17, 2018, claiming priorities based on Japanese Patent Application Nos. 2017-116692 filed Jun. 14, 2017 and 2017-146807 filed Jul. 28, 2017.

TECHNICAL FIELD

The present invention relates to a dose determination program and a dose determination device, each of which determines a dose of an erythropoiesis-stimulating agent.

BACKGROUND ART

Since production of erythrocytes in a bone marrow is stimulated by erythropoietin mainly produced in a kidney, it has been conventionally known that no erythropoietin or a very decreased amount of erythropoietin is generated in a renal failure patient with a deteriorated kidney and production of erythrocytes is therefore suppressed in such a renal failure patient, thus resulting in a high degree of anemia, so-called renal anemia.

In order to supplement erythropoietin to a patient with renal anemia such as a dialysis patient, an erythropoiesis-stimulating agent (ESA), which is an erythropoietin formulation produced through genetic recombination, is administered to such a patient. The ESA includes: a first-generation medicament such as epoetin α or epoetin β (EPO); and a second-generation medicament such as darbepoetin α (DA). These medicaments are administered to dialysis patients by intravenous injection through blood circuits upon end of dialysis, for example. It should be noted that a dose of the ESA on this occasion is appropriately determined based on a doctor's experience to attain an adequate blood hemoglobin concentration (10 to 11 g/dL) as determined in a medical society guideline; however, since the dose of the ESA is determined based on the doctor's experience, the dose of the ESA may become too large or small, with the result that the hemoglobin concentration in blood cannot be avoided from being fluctuated greatly. It has been difficult to reduce a range of the fluctuation.

Meanwhile, when the dose of such an ESA is increased to result in a high hemoglobin concentration, the following problems arise: treatment cost is increased due to an increased amount of use of the ESA, which is expensive; and an influence on the human body is increased. On the other hand, when the blood hemoglobin concentration becomes too low due to a small dose of the ESA, the influence on the human body is also increased, disadvantageously.

In order to solve the problems in the above-described method that is based on the doctor's experience, an algorithm has been made in which the dose of the ESA is determined in accordance with a difference between a target hemoglobin concentration and a hemoglobin concentration at the present time in the case where the hemoglobin concentration is measured once every two weeks. In other words, when the hemoglobin concentration at the present time is lower than the target hemoglobin concentration, the dose of the ESA is increased in accordance with the difference therebetween, whereas when the hemoglobin concentration at the present time is higher than the target hemoglobin concentration, the dose of the ESA is decreased in accordance with the difference therebetween (see Non-Patent Literature 1). However, with such a method, the actually measured hemoglobin concentration is actually fluctuated to be much larger than and much smaller than the target hemoglobin concentration.

Further, the following method is employed: first, assuming that there is a logarithmic relation between a hemoglobin production rate at the present time and a concentration of an erythropoiesis-stimulating agent in a body until the present time, a concentration of the erythropoiesis-stimulating agent in the body for attaining the target hemoglobin production rate is calculated using a simple logarithmic expression; and a corresponding dose of the erythropoiesis-stimulating agent is then determined based on the concentration thereof in the body (Non-Patent Literature 1).

However, this method is complicated because the hemoglobin production rate is first calculated, the concentration of the erythropoiesis-stimulating agent in the body is then calculated based on the hemoglobin production rate, and the dose of the erythropoiesis-stimulating agent is finally calculated based on the concentration of the erythropoiesis-stimulating agent in the body.

Further, in the calculation of the hemoglobin production rate in this method, the logarithmic value of the concentration of the erythropoiesis-stimulating agent in the body is simply assumed to be linearly proportional to the hemoglobin production rate. Hence, in a region in which the concentration of the erythropoiesis-stimulating agent in the body is low, the relation between the hemoglobin production rate and the concentration of the erythropoiesis-stimulating agent in the body until the present time does not coincide with the given function expression, thus resulting in an error in the hemoglobin production rate.

In WO2014/200054 (Patent Literature 1), a hemoglobin production rate (in other words, a target hemoglobin production rate) under a target hemoglobin concentration is calculated based on the target hemoglobin concentration, and a concentration of an ESA in serum for attaining the target hemoglobin production rate is then calculated based on a relation between a hemoglobin production rate at the present time and a concentration of the ESA until the present time. Then, a dose of the ESA for attaining the concentration of the ESA is calculated based on the relation between the concentration of the ESA and the dose of the ESA so as to determine a dose of the ESA for attaining the target hemoglobin concentration.

However, also when the method for determining the dose of the ESA as disclosed in Patent Literature 1 is used, the algorithm is complicated because the hemoglobin production rate is calculated, the concentration of the ESA is calculated based on the hemoglobin production rate, and then the dose of the ESA is calculated based on the concentration of the ESA.

CITATION LIST

Patent Literature

PTL 1: WO2014/200054

Non Patent Literature

NPL 1: Fishbane S, et al.: Kidney Int. 68: 1337-1343, 2005.

SUMMARY OF INVENTION

Technical Problem

Here, the present invention has been made in view of such a circumstance, and has an object to provide a dose determination program and a dose determination device, by each of which a dose of an erythropoiesis-stimulating agent can be determined to reduce a range of fluctuation of a hemoglobin concentration in blood by stably maintaining the hemoglobin concentration in blood at a target value.

Solution to Problem

A dose determination program according to the present invention is a dose determination program for an erythropoiesis-stimulating agent, the dose determination program being executable by a computer, the dose determination program causing the computer to perform: obtaining a predetermined target hemoglobin concentration; obtaining a first concentration and a first dose in a stable state in which a hemoglobin concentration is stable at the first concentration by repeatedly administering the first dose a plurality of times; and calculating a second dose of the erythropoiesis-stimulating agent based on the obtained target hemoglobin concentration, the obtained first concentration, and the obtained first dose, the second dose of the erythropoiesis-stimulating agent being to be administered by a fixed amount.

Preferably in the dose determination program according to the present invention, in the calculating of the second dose, the second dose is calculated using a predetermined correlation between the second dose and each of the first concentration, the first dose, and the target hemoglobin concentration.

Preferably in the dose determination program according to the present invention, the correlation is calculated based on a first relational expression between the first concentration and the first dose in the stable state and a second relational expression between the target hemoglobin concentration and the second dose in a state in which the hemoglobin concentration is stable at the target hemoglobin concentration.

Preferably in the dose determination program according to the present invention, in the first relational expression, a logarithmic value of a value obtained by multiplying, by a second coefficient, a value obtained by adding a first coefficient to the first dose, and the first concentration in the stable state are proportional to each other, and in the second relational expression, a logarithmic value of a value obtained by multiplying, by the second coefficient, a value obtained by adding the first coefficient to the second dose, and the target hemoglobin concentration in the state in which the hemoglobin concentration is stable at the target hemoglobin concentration are proportional to each other.

Preferably in the dose determination program according to the present invention, the first coefficient and the second coefficient differ depending on a case where a patient is in a course of increasing a dose of the erythropoiesis-stimulating agent and a case where the patient is in a course of decreasing the dose of the erythropoiesis-stimulating agent.

Preferably in the dose determination program according to the present invention, in a case where the erythropoiesis-stimulating agent to be administered is epoetin alfa or epoetin beta, where a unit of a dose of the erythropoiesis-stimulating agent is unit/week and where a patient is in a course of increasing the dose of the erythropoiesis-stimulating agent, when the first coefficient is represented by Ka1, the second coefficient is represented by Kb1, and the first coefficient Ka1 falls within a range of $0 \leq Ka1 \leq 2700$, a value of the second coefficient Kb1 is calculated based on the following formula (1) using the first coefficient Ka1:

$$Kb1 = 4 \times 10^{-17} \times Ka1^6 - 4 \times 10^{-13} \times Ka1^5 + 10^{-9} \times Ka1^4 - 3 \times 10^{-6} \times Ka1^3 + 0.0029 \times Ka1^2 - 1.4755 \times Ka1 + 304.49 \quad \text{Formula (1)}.$$

Preferably in the dose determination program according to the present invention, in a case where the erythropoiesis-stimulating agent to be administered is epoetin alfa or epoetin beta, where a unit of a dose of the erythropoiesis-stimulating agent is unit/week and where a patient is in a course of decreasing the dose of the erythropoiesis-stimulating agent, when the first coefficient is represented by Ka2, the second coefficient is represented by Kb2, and the first coefficient Ka2 falls within a range of $0 \leq Ka2 \leq 4800$, a value of the second coefficient Kb2 is calculated based on the following formula (2) using the first coefficient Ka2:

$$Kb2 = -2 \times 10^{-17} \times Ka2^5 + 4 \times 10^{-13} \times Ka2^4 - 2 \times 10^{-9} \times Ka2^3 + 6 \times 10^{-6} \times Ka2^2 - 0.0086 \times Ka2 + 4.8389 \quad \text{Formula (2)}.$$

Preferably in the dose determination program according to the present invention, in a case where the erythropoiesis-stimulating agent to be administered is darbepoetin alfa, where a unit of a dose of the erythropoiesis-stimulating agent is μg/week and where a patient is in a course of increasing the dose of the erythropoiesis-stimulating agent, when the first coefficient is represented by Ka3, the second coefficient is represented by Kb3, and the first coefficient Ka3 falls within a range of $0 \leq Ka3 \leq 11$, a value of the second coefficient Kb3 is calculated based on the following formula (3) using the first coefficient Ka3:

$$Kb3 = 0.0564 \times Ka3^2 - 1.0544 \times Ka + 7.2527 \quad \text{Formula (3)}.$$

Preferably in the dose determination program according to the present invention, in a case where the erythropoiesis-stimulating agent to be administered is darbepoetin alfa, where a unit of a dose of the erythropoiesis-stimulating agent is μg/week and where a patient is in a course of decreasing the dose of the erythropoiesis-stimulating agent, when the first coefficient is represented by Ka4, the second coefficient is represented by Kb4, and the first coefficient Ka4 falls within a range of $41 \leq Ka4 \leq 60$, a value of the second coefficient Kb4 is calculated based on the following formula (4) using the first coefficient Ka4:

$$Kb4 = -75.67 \times Ka4^5 + 22123 \times Ka4^4 - 3 \times 10^6 \times Ka4^3 + 10^8 \times Ka4^2 - 4 \times 10^9 \times Ka4 + 5 \times 10^{10} \quad \text{Formula (4)}$$

In the dose determination program according to the present invention, the second coefficient may be represented by a first-degree equation of the first coefficient.

Preferably in the dose determination program according to the present invention, in a case where the erythropoiesis-stimulating agent to be administered is epoetin alfa or epoetin beta, where a unit of a dose of the erythropoiesis-stimulating agent is unit/week and where a patient is in a course of increasing the dose of the erythropoiesis-stimulating agent, when the first coefficient is represented by Ka1, the second coefficient is represented by Kb1, and the first coefficient Ka1 falls within a range of 600≤Ka1≤1000, a value of the second coefficient Kb1 is calculated based on the following formula (5) using the first coefficient Ka1:

$$Kb1=-0.016\times Ka1+19.8 \quad \text{Formula (5).}$$

In the dose determination program according to the present invention, the second coefficient may be represented by a second-degree equation of the first coefficient.

Preferably in the dose determination program according to the present invention, in a case where the erythropoiesis-stimulating agent to be administered is epoetin alfa or epoetin beta, where a unit of a dose of the erythropoiesis-stimulating agent is unit/week and where a patient is in a course of decreasing the dose of the erythropoiesis-stimulating agent, when the first coefficient is represented by Ka2, the second coefficient is represented by Kb2, and the first coefficient Ka2 falls within a range of 100≤Ka2≤1000, a value of the second coefficient Kb2 is calculated based on the following formula (6) using the first coefficient Ka2:

$$Kb2=(0.0002\times Ka2^2-0.6226\times Ka2+444.25)/100 \quad \text{Formula (6).}$$

Preferably in the dose determination program according to the present invention, in a case where the erythropoiesis-stimulating agent to be administered is darbepoetin alfa, where a unit of a dose of the erythropoiesis-stimulating agent is μg/week and where a patient is in a course of decreasing the dose of the erythropoiesis-stimulating agent, when the first coefficient is represented by Ka4, the second coefficient is represented by Kb4, and the first coefficient Ka4 falls within a range of 45≤Ka4≤50, a value of the second coefficient Kb4 is calculated based on the following formula (7) using the first coefficient Ka4:

$$Kb4=(0.7321\times Ka4^2-72.325\times Ka4+1790.6)\times 1000000 \quad \text{Formula (7).}$$

A dose determination device according to the present invention is a dose determination device that determines a dose of an erythropoiesis-stimulating agent, the dose determination device including: a first obtaining unit that obtains a predetermined target hemoglobin concentration; a second obtaining unit that obtains a first concentration and a first dose in a stable state in which a hemoglobin concentration is stable at the first concentration by repeatedly administering the first dose a plurality of times; and a calculation unit that calculates a second dose of the erythropoiesis-stimulating agent based on the obtained target hemoglobin concentration, the obtained first concentration, and the obtained first dose, the second dose of the erythropoiesis-stimulating agent being to be administered by a fixed amount.

Advantageous Effects of Invention

According to the present invention, there can be provided a dose determination program and a dose determination device, by each of which a dose of an erythropoiesis-stimulating agent can be determined to reduce a range of fluctuation of a hemoglobin concentration in blood by stably maintaining the hemoglobin concentration in blood at a target value.

DESCRIPTION OF EMBODIMENTS

Figure 1:
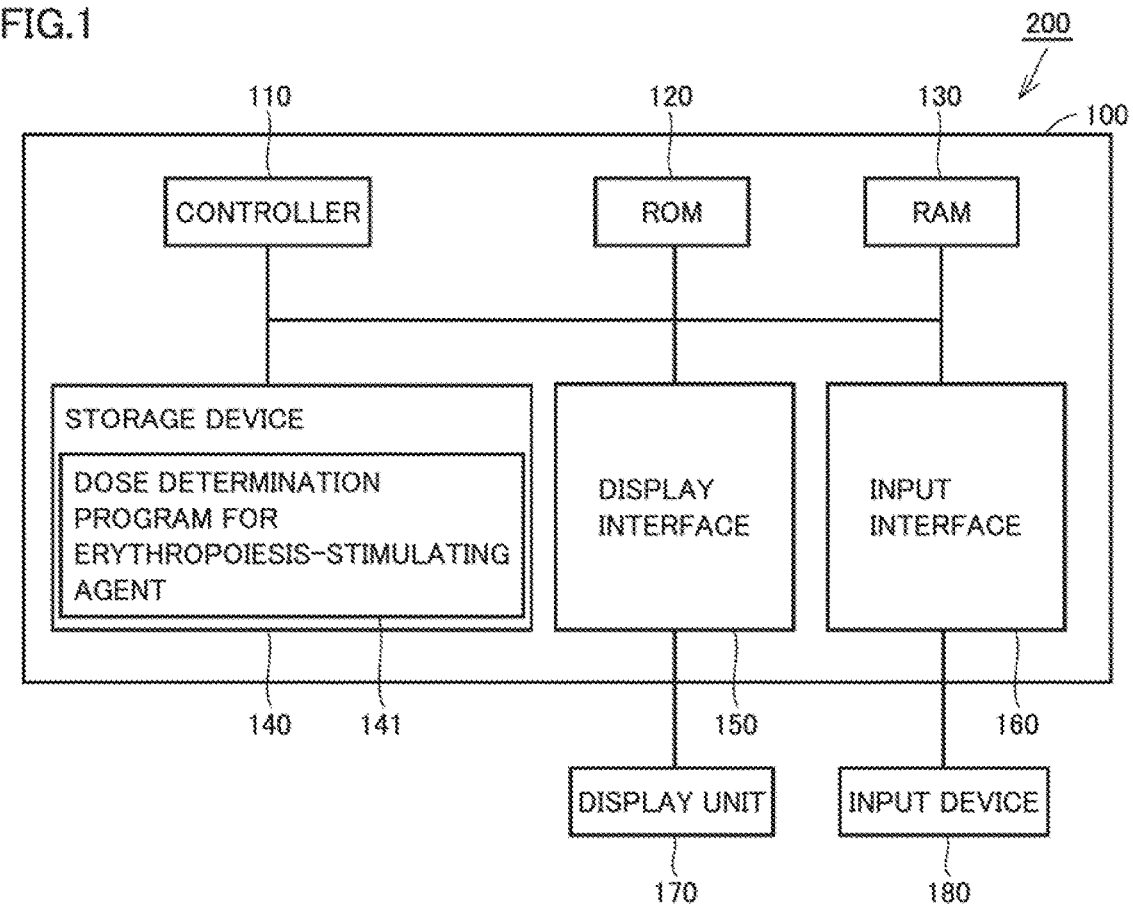
FIG. 1 is a block diagram showing a configuration of hardware in which a dose determination device according to an embodiment is incorporated.

The following describes embodiments of the present invention in detail with reference to figures. It should be noted that in the embodiments described below, the same or common portions are given the same reference characters in the figures and are not described repeatedly.

(Hardware and Dose Determination Device)

FIG. 1 is a block diagram showing a configuration of hardware in which a dose determination device according to an embodiment is incorporated. With reference to FIG. 1, hardware 200 in which a dose determination device 100 according to the embodiment is incorporated will be described.

As shown in FIG. 1, hardware 200 includes a dose determination device 100, a display unit 170, and an input device 180.

Display unit 170 includes a liquid crystal display, an organic EL (Electro Luminescence) display, another display device, or the like, for example. Input device 180 includes various types of input keys including numeric keys, a touch sensor, or the like.

Dose determination device 100 includes a controller 110, a ROM (Read Only Memory) 120, a RAM (Random Access Memory) 130, a storage device 140, a display interface 150, an input interface 160, display unit 170, and input device 180.

Controller 110 is constituted of at least one integrated circuit, for example. The integrated circuit is constituted of at least one CPU (Central Processing Unit), at least one ASIC (Application Specific Integrated Circuit), at least one FPGA (Field Programmable Gate Array), a combination thereof, or the like, for example.

Controller 110 executes a dose determination program 141 described later. Based on reception of an execution instruction of dose determination program 141, controller 110 reads out dose determination program 141 from storage device 140 to ROM 120. RAM 130 functions as a working memory, and temporarily stores various types of data required to execute dose determination program 141.

Storage device 140 stores dose determination program 141 and the like. It should be noted that the storage location of dose determination program 141 is not limited to storage device 140, and dose determination program 141 may be stored in ROM 120, RAM 130, an external storage device, or the like, for example.

It should be noted that dose determination program 141 may be provided to be included in part of an appropriate program, rather than an individual program. In this case, a dose determination process according to the present embodiment is implemented in cooperation with the appropriate program. Even such a program that does not include parts of modules is not deviated from the gist of dose determination device 100 according to the present embodiment.

Further, part or whole of functions provided by dose determination program 141 according to the present embodiment may be implemented by dedicated hardware. Further, part or whole of the functions provided by dose determination program 141 may be implemented by cooperation of dose determination device 100 and a server provided external to dose determination device 100. Further, dose determination device 100 may be configured in the form of a so-called cloud service in which at least one server implements a process according to the present embodiment.

Figure 2:
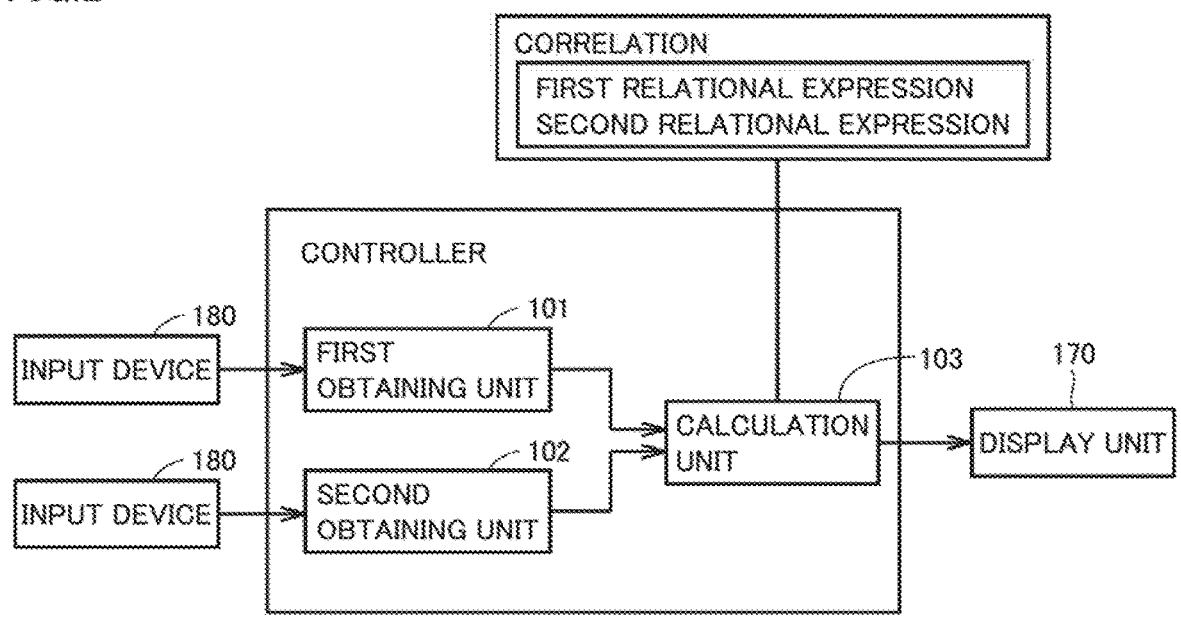
FIG. 2 is a block diagram showing a functional configuration of the dose determination device according to the embodiment.

FIG. 2 is a block diagram showing a functional configuration of the dose determination device according to the embodiment. With reference to FIG. 2, the functional configuration of dose determination device 100 according to the embodiment will be described.

As shown in FIG. 2, as the functional configuration, dose determination device 100 includes a first obtaining unit 101, a second obtaining unit 102, and a calculation unit 103.

First obtaining unit 101 obtains a predetermined target hemoglobin concentration. For example, first obtaining unit 101 obtains a target hemoglobin concentration from input device 180. It should be noted that when the target hemoglobin concentration is input in advance and is stored in a storage location such as storage device 140, ROM 120, or RAM 130, first obtaining unit 101 may obtain the target hemoglobin concentration from the storage location.

The target hemoglobin concentration is a value falling within a desired hemoglobin concentration range defined in a guideline of Japanese Society for Dialysis Therapy. In the guideline, hemoglobin concentrations are preferably distributed within a range of more than or equal to 10.0 g/dL and less than or equal to 11.0 g/dL. Hence, the above-described target hemoglobin concentration may be set to 10.5 g/dL, for example.

Second obtaining unit 102 obtains a first concentration and a first dose in a first stable state in which a hemoglobin concentration is stable at the first concentration by repeatedly administering the first dose a plurality of times. For example, second obtaining unit 102 obtains the first concentration and the first dose from input device 180. It should be noted that when the first concentration and the first dose are input in advance and are stored in a storage location such as storage device 140, ROM 120, or RAM 130, second obtaining unit 102 may obtain the first concentration and the first dose from the storage location.

Calculation unit 103 calculates a second dose of the erythropoiesis-stimulating agent based on the obtained target hemoglobin concentration, the obtained first concentration, and the obtained first dose, the second dose of the erythropoiesis-stimulating agent being to be administered by a fixed amount. More particularly, calculation unit 103 calculates the second dose using a predetermined correlation between the second dose and each of the first concentration, the first dose, and the target hemoglobin concentration. It should be noted that the above-described correlation will be described later with reference to FIG. 3 and FIG. 4.

Figure 3:
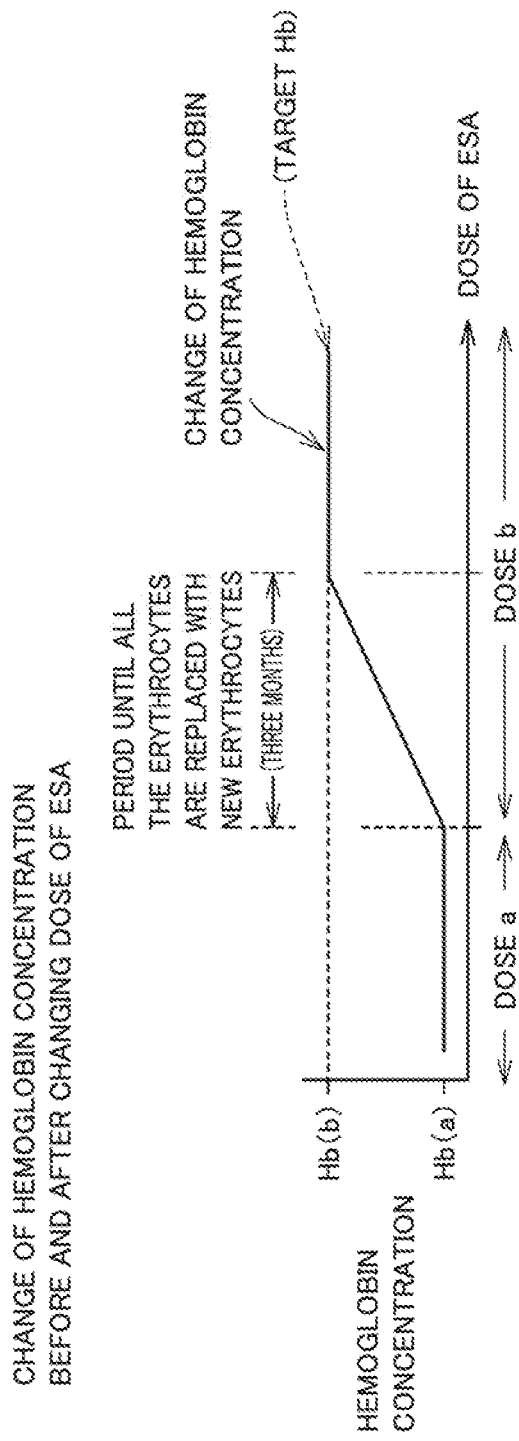
FIG. 3 shows a change of a hemoglobin concentration before and after changing a dose of an erythropoiesis-stimulating agent.

FIG. 3 shows a change of the hemoglobin concentration before and after changing the dose of the erythropoiesis-stimulating agent. With reference to FIG. 3, the following describes the change of the hemoglobin concentration before and after changing the dose of the erythropoiesis-stimulating agent.

As shown in FIG. 3, when a constant dose a (first dose) of the erythropoiesis-stimulating agent is continuously administered, the hemoglobin concentration becomes stable at a concentration Hb (a) (first concentration) corresponding to the dose. In this stable state (first stable state), when the dose of the erythropoiesis-stimulating agent is changed to a constant dose b (second dose) and this dose b is continuously administered, the hemoglobin concentration is increased. After about three months, which correspond to an average erythrocyte life, since dose b was continuously administered, the hemoglobin concentration becomes stable at a concentration Hb (b) corresponding to dose b.

In the present embodiment, by executing the dose determination program with the above-described concentration Hb (b) being set as the target hemoglobin concentration, dose b (second dose) is calculated based on a predetermined correlation between dose b (second dose) and each of predetermined dose a (first dose), concentration Hb (a) (first concentration), and the target hemoglobin concentration.

Here, as described above, when a certain constant amount of the erythropoiesis-stimulating agent is continuously administered and the hemoglobin concentration is stable at a predetermined value, a predetermined relational expression must be satisfied between the hemoglobin concentration and the dose of the erythropoiesis-stimulating agent in the stable state.

If the above-described relational expression has only two variables, i.e., the hemoglobin concentration and the dose of the erythropoiesis-stimulating agent, a recommended dose (second dose) of the erythropoiesis-stimulating agent corresponding to the target hemoglobin concentration can be calculated readily under a condition that the target hemoglobin concentration is given.

However, actually, an element that determines the hemoglobin concentration in the stable state is not only the dose of the erythropoiesis-stimulating agent, and the hemoglobin concentration is also influenced by reactivity of a hemopoietic tissue to the erythropoiesis-stimulating agent.

In other words, the above-described relational expression satisfied between the hemoglobin concentration and the dose of the erythropoiesis-stimulating agent in the stable state has three variables, i.e., the hemoglobin concentration (Hb), the dose (D) of the erythropoiesis-stimulating agent, and the reactivity ($\beta$) of the hemopoietic tissue, as indicated in the following formula (A1):

$$Hb = f(\beta, D) \quad \text{Formula (A1)}$$

Hence, in order to calculate the recommended dose (second dose) of the erythropoiesis-stimulating agent for attaining the target hemoglobin concentration, for the above-described relational expression, two relational expressions respectively satisfied in two different stable states are required.

When it is assumed that one of the two relational expressions is a relational expression satisfied at the present time (first state in which the concentration is stable at the first concentration) at which the recommended dose is to be determined, the relational expression is represented by the following formula (A2) having variables, i.e., a hemoglobin concentration (cHb) at the present time, a dose (cD) of the erythropoiesis-stimulating agent administered by a fixed amount until the present time, and the reactivity ($\beta$) of the hemopoietic tissue:

$$cHb = f(\beta, cD) \quad \text{Formula (A2)}$$

When it is assumed that the other of the two relational expressions is a relational expression satisfied in a state in which the hemoglobin concentration is stable at the target hemoglobin concentration, the relational expression is represented by the following formula (A3) having variables, i.e., the target hemoglobin concentration (tHb), the recommended dose (rD), and the reactivity ($\beta$) of the hemopoietic tissue:

$$tHb = f(\beta, rD) \quad \text{Formula (A3)}$$

In these formulas (A2) and (A3), the target hemoglobin concentration (tHb), the hemoglobin concentration (cHb) at the present time, and the dose (cd) of the erythropoiesis-stimulating agent administered by the fixed amount until the present time are given, whereas the recommended dose (rD) and the reactivity ($\beta$) of the hemopoietic tissue are unknown. Therefore, by solving these formulas (A2) and (A3) simultaneously, the recommended dose (rD) can be calculated.

That is, by simultaneously solving the first relational expression between the first concentration and the first dose in the first stable state and the second relational expression between the target hemoglobin concentration and the second dose in the state in which the hemoglobin concentration is stable at the target hemoglobin concentration, the correlation between the second dose and each of the first concentration, the first dose and the target hemoglobin concentration is obtained.

In order to calculate the recommended dose (rD) using the above-described correlation, more specific relational expressions for the hemoglobin concentration, the dose (D) of the erythropoiesis-stimulating agent, and the reactivity (β) of the hemopoietic tissue in the stable state are required.

In the present embodiment, the specific relational expressions are derived by evolving an in vitro experimental result by Nagano et al.

Nagano et al., have reported that when marrow cells are cultured in culture fluids including various concentrations of erythropoiesis-stimulating agent, colony-forming unit-erythrocyte (CFU-E) colonies are formed after one week, and in a predetermined concentration range of the erythropoiesis-stimulating agent, the number of the formed colonies and the logarithmic value of the concentration of the erythropoiesis-stimulating agent in a culture fluid are in a linear relation (see Nobuo Nagano et al., "Kidney and Dialysis", 60 (6), 1039-1046, 2006).

Figure 4:
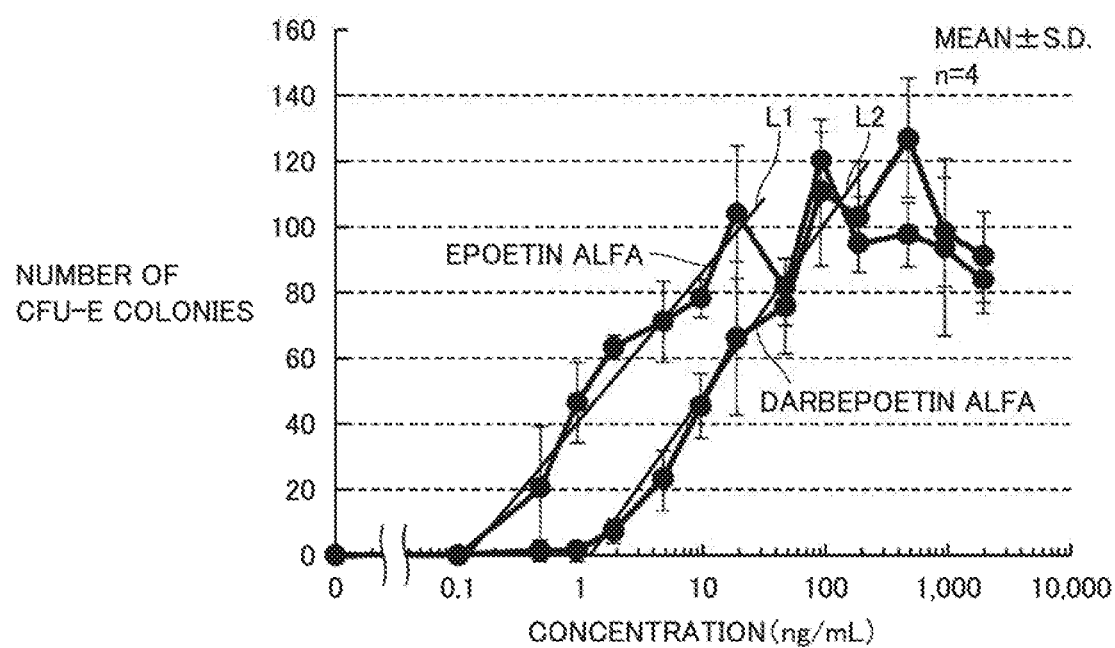
FIG. 4 shows an experimental result by Nagano et al., and shows a relation between a logarithmic value of a concentration of the erythropoiesis-stimulating agent in a culture fluid and the number of formed colony-forming unit-erythrocyte (CFU-E) colonies.

FIG. 4 shows the experimental result by Nagano et al., and shows a relation between the logarithmic value of the concentration of the erythropoiesis-stimulating agent in the culture fluid and the number of the formed colony-forming unit-erythrocyte (CFU-E) colonies. For example, irrespective of whether the erythropoiesis-stimulating agent is epoetin alfa or darbepoetin alfa, the relation between the logarithmic value of the concentration of the erythropoiesis-stimulating agent in the culture fluid and the number of the formed colony-forming unit-erythrocyte (CFU-E) colonies are in a linear relation in a predetermined range as indicated by solid lines L1, L2 in FIG. 4.

Meanwhile, since the colony-forming unit-erythrocytes will differentiate to erythrocytes, it can be said that the number of the colony-forming unit-erythrocyte colonies is in a linear relation with the concentration of hemoglobin to be subsequently formed. Further, it can be said that the concentration of the erythropoiesis-stimulating agent in the culture fluid is in a linear relation with the amount of the erythropoiesis-stimulating agent added to the culture fluid.

In consideration of these relations, the following concept is derived from the in vitro experimental result by Nagano et al., in which the number of the colony-forming unit-erythrocyte (CFU-E) colonies is in a linear relation with the logarithmic value of the concentration of the erythropoiesis-stimulating agent in the culture fluid: the blood hemoglobin concentration in the patient is in a linear relation with the logarithmic value of the dose of the erythropoiesis-stimulating agent. However, when this concept is applied to a dialysis patient, this concept needs to be modified to some extent.

In a dialysis patient's body, haemopoiesis is stimulated by not only an administered erythropoiesis-stimulating agent but also various levels of endogenous erythropoietin produced from a deteriorated kidney or an organ other than the kidney. Hence, in the present embodiment, for the dialysis patient, the above-described concept is modified as follows: the hemoglobin concentration is in a linear relation with the logarithmic value of the "sum of the dose of the erythropoiesis-stimulating agent and a production amount of the endogenous erythropoietin".

Figure 5:
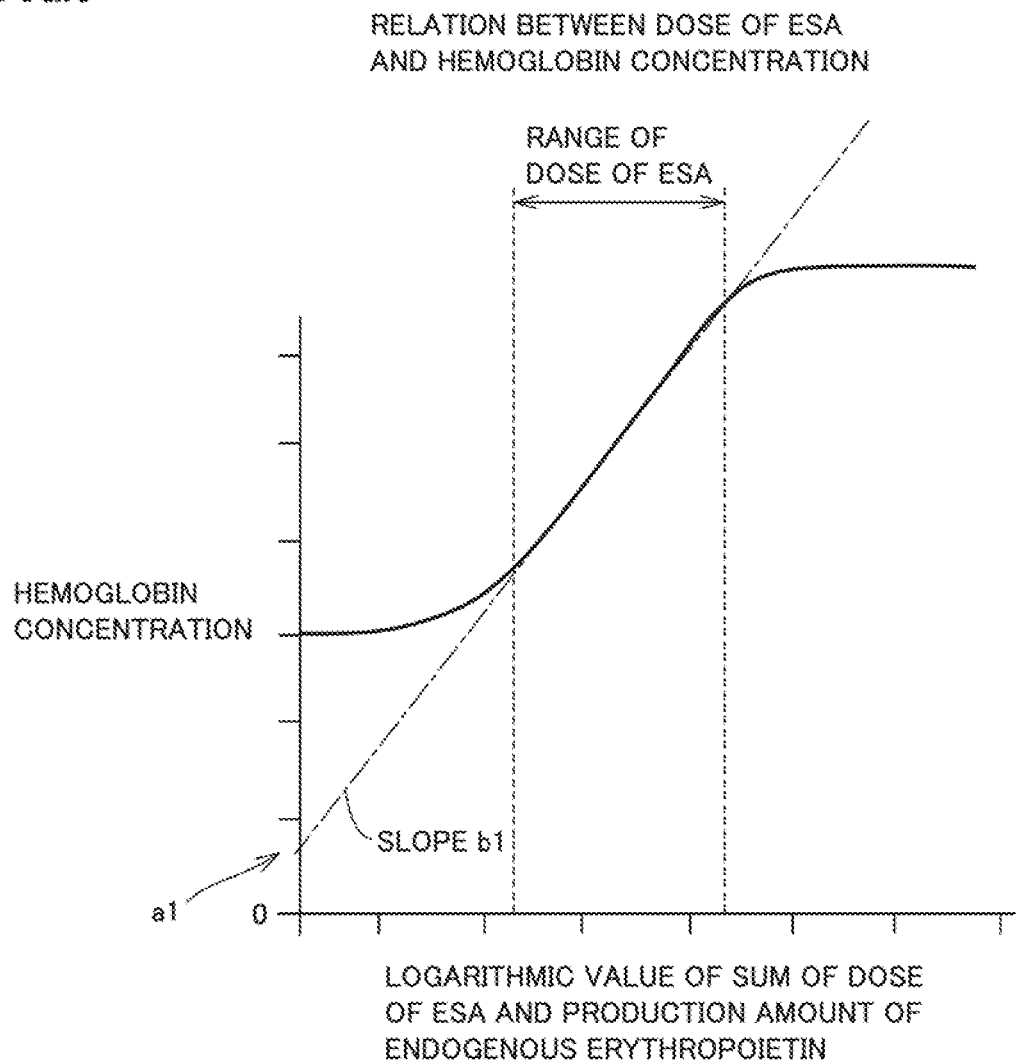
FIG. 5 shows a relation between the hemoglobin concentration and a logarithmic value of the sum of the dose of the erythropoiesis-stimulating agent and a production amount of endogenous erythropoietin.

FIG. 5 shows a relation between the hemoglobin concentration and the logarithmic value of the sum of the dose of the erythropoiesis-stimulating agent and the production amount of the endogenous erythropoietin. FIG. 5 shows that the content of FIG. 4 obtained from the experimental result by Nagano et al., is modified based on such a concept that the hemoglobin concentration is in a linear relation with the logarithmic value of the "sum of the dose of the erythropoiesis-stimulating agent and the production amount of the endogenous erythropoietin" as described above.

As shown in FIG. 5, in a clinical administration range, the hemoglobin concentration is in a linear relation with the logarithmic value of the "sum of the dose of the erythropoiesis-stimulating agent and the production amount of the endogenous erythropoietin".

In the above-described administration range, the relation between hemoglobin concentration Hb and the above-described logarithmic value can be represented by the following formula (A4) employing a slope b1, an intercept a1, dose D of the erythropoiesis-stimulating agent, and production amount G of the endogenic erythropoietin:

$$Hb = b1 \times \ln(D+G) + a1 \qquad \text{Formula (A4)}$$

Further, the formula (A4) can be rewritten to the following formula (A5):

$$Hb = b1 \times \ln[(D+G) \times e^{(a1/b1)}] \qquad \text{Formula (A5)}$$

Here, hemoglobin concentration Hb and dose D are variables that can differ in values depending on times in the same patient. Moreover, the above-described slope b1 represents reactivity of the bone marrow to the erythropoiesis-stimulating agent and the endogenous erythropoietin. This b1, production amount G of the endogenous erythropoietin, and intercept a1 are values that differ among patients. On the other hand, each of b1, production amount G of the endogenous erythropoietin, and intercept a1 is substantially constant in the one patient with passage of time, and can be employed as a constant.

Hence, $e^{(a1/b1)}$ in the above-described formula (A5) can be handled as one constant F. Hence, the above-described formula (A5) can be represented by the following formula (A6):

$$Hb = b1 \times \ln[(D+G) \times F] \qquad \text{Formula (A6)}$$

Here, when a hemoglobin concentration Hb1 at a certain time in the stable state, and a dose D1 of the erythropoiesis-stimulating agent administered at the certain time in the stable state are substituted into the formula (A6), the following formula (A7) is obtained:

$$Hb1 = b1 \times \ln[(D1+G) \times F] \qquad \text{Formula (A7)}$$

Likewise, when a hemoglobin concentration Hb2 in the stable state three months after changing the dose and a recommended dose Drec of the erythropoiesis-stimulating agent are substituted into the formula (A6), the following formula (A8) is obtained:

$$Hb2 = b1 \times \ln[(Drec+G) \times F] \qquad \text{Formula (A8)}$$

By solving the formula (A7) and the formula (A8) simultaneously, the following formula (A9) is obtained.

$$Drec = \frac{[(D1+G) \times F]^{(Hb2/Hb1)}}{F} - G \qquad \text{Formula (A9)}$$

Here, production amount G of the endogenous erythropoietin and constant F above have substantially constant values in the same patient with passage of time as described above, but are varied among different patients. Hence, theoretically, it is ideal to determine production amount G of the endogenous erythropoietin and constant F for each patient and derive a formula for calculating a recommended dose for each patient based on them.

However, it is unrealistic to determine production amount G of the endogenous erythropoietin and constant F for each patient.

Hence, in the present embodiment, it is programmed to calculate a more accurate recommended dose using a first coefficient Ka and a second coefficient Kb common among a plurality of patients instead of production amount G of the endogenous erythropoietin and constant F.

The following describes a method for determining each of first coefficient Ka and second coefficient Kb. A patient for whom a dose of erythropoiesis-stimulating agent is being increased in order to reach a target hemoglobin concentration has a small production amount of endogenous erythropoietin, and is in a course of supplementing this with the erythropoiesis-stimulating agent to be administered. On the other hand, it is considered that a patient for whom a dose of erythropoiesis-stimulating agent is being decreased in order to reach a target hemoglobin concentration has a large production amount of endogenous erythropoietin, and is in a course of decreasing an excessively administered erythropoiesis-stimulating agent.

Therefore, first coefficient Ka corresponding to the production amount of the endogenous erythropoietin and second coefficient Kb associated with first coefficient Ka are preferably determined for each of the following cases: a case where the patient is in the course of increasing the dose of the erythropoiesis-stimulating agent; and a case where the patient is in the course of decreasing the dose of the erythropoiesis-stimulating agent.

First coefficient Ka and second coefficient Kb can be determined by analyzing past data of the plurality of patients.

When the patient is in the course of increasing the dose of the erythropoiesis-stimulating agent, irrespective of whether the erythropoiesis-stimulating agent is epoetin or darbepoetin, data in the following case is extracted from pieces of past data of a multiplicity of patients: the dose of the erythropoiesis-stimulating agent was constant for three or more months, the dose of the erythropoiesis-stimulating agent was increased twice or more in a certain month, and the dose of the erythropoiesis-stimulating agent was then unchanged for three or more months.

When the patient is in the course of decreasing the dose of the erythropoiesis-stimulating agent, irrespective of whether the erythropoiesis-stimulating agent is epoetin or darbepoetin, data in the following case is extracted from pieces of past data of a multiplicity of patients: the dose of the erythropoiesis-stimulating agent was constant for three or more months, the dose of the erythropoiesis-stimulating agent was decreased to be ½ or less in a certain month, and the dose of the erythropoiesis-stimulating agent was then unchanged for three or more months.

First coefficient Ka and second coefficient Kb common among all the patients are determined by analyzing the past data based on the following theory.

When the dose of the erythropoiesis-stimulating agent has been unchanged for three or more months, dynamics of hemoglobin becomes a stationary state (first stable state). Then, when another three months has passed after the dose of the erythropoiesis-stimulating agent is changed greatly, the dynamics of hemoglobin reaches a new stationary state (second stable state).

When a relational expression, including first coefficient Ka and second coefficient Kb, between the hemoglobin concentration and the dose of the erythropoiesis-stimulating agent is given, various values can be substituted into first coefficient Ka and second coefficient Kb so as to calculate the dose of the erythropoiesis-stimulating agent in the second stable state based on the hemoglobin concentration and the dose of the erythropoiesis-stimulating agent in the first stable state and the hemoglobin concentration in the second stable state.

Then, by comparing the calculated dose of the erythropoiesis-stimulating agent in the second stable state with the actual dose of the erythropoiesis-stimulating agent, a difference therebetween is calculated. From the various values substituted to first coefficient Ka and second coefficient Kb, values are determined to attain the minimum average value of the above-described differences among the plurality of patients. Accordingly, optimum first coefficient Ka and second coefficient Kb are determined.

Specifically, they are determined as follows. In a range in which the erythropoiesis-stimulating agent is clinically administered, the relation between the hemoglobin concentration (Hb) and the dose (D) of the erythropoiesis-stimulating agent is represented by the formula (A6) as described above. Here, production amount G of the endogenous erythropoietin and constant F in the formula (A6) are respectively replaced with first coefficient Ka and second coefficient Kb common among the plurality of patients, thereby obtaining the following formula (A10):

$$Hb = b1 \times \ln[(D+Ka) \times Kb] \quad \text{Formula (A10)}$$

Next, the formula (A10) is applied to the dynamics of hemoglobin in the month in which the dose of the erythropoiesis-stimulating agent was changed, thereby obtaining the following formula (A11). It should be noted that Hb1 represents the hemoglobin concentration in the stationary state (first stable state) before changing the dose of the erythropoiesis-stimulating agent, and D1 represents the dose of the erythropoiesis-stimulating agent administered before changing the dose of the erythropoiesis-stimulating agent.

$$Hb1 = b1 \times \ln[(D1+Ka) \times Kb] \quad \text{Formula (A11)}$$

Likewise, the formula (A10) is applied to the dynamics of hemoglobin three months after changing the dose of the erythropoiesis-stimulating agent, thereby obtaining the following formula (A12). It should be noted that Hb2 represents the hemoglobin concentration in the stationary state (second stable state) after changing the dose of the erythropoiesis-stimulating agent, and D2 represents the dose of the erythropoiesis-stimulating agent in the stationary state.

$$Hb2 = b1 \times \ln[(D2+Ka) \times Kb] \quad \text{Formula (A12)}$$

By simultaneously solving the formula (A11) and the formula (A12), the following formula (A13) is obtained:

$$D2 = \frac{[(D1+Ka) \times Kb]^{(Hb2/Hb1)}}{Kb} - Ka \quad \text{Formula (A13)}$$

Here, various values are substituted into Ka and Kb for each of the plurality of patients and the dose of the erythropoiesis-stimulating agent is changed, whereby dose D2 of the erythropoiesis-stimulating agent after three months is calculated. An absolute value A of an error between the calculated dose of the erythropoiesis-stimulating agent and the actually administered dose of the erythropoiesis-stimulating agent is calculated by the following formula (A14). It should be noted that in the formula (A14), D2cal represents the above-calculated dose of the erythropoiesis-stimulating agent, and D2mea represents the actually administered dose of the erythropoiesis-stimulating agent.

$$A = \frac{|D2cal - D2mea|}{D2mea} \quad \text{Formula (A14)}$$

The above-described A value is calculated for each of all the target patients for the following cases: a case where the patient is in the course of increasing the dose of the erythropoiesis-stimulating agent; and a case where the patient is in the course of decreasing the dose of the erythropoiesis-stimulating agent. An average thereof is used as an error value. From the various values substituted into Ka and Kb, values allowing for the minimum error value are determined and these are employed as first coefficient Ka and second coefficient Kb for providing an accurate recommended dose of the erythropoiesis-stimulating agent.

It should be noted that first coefficient Ka and second coefficient Kb have different values depending on the case where the patient is in the course of increasing the dose of the erythropoiesis-stimulating agent and the case where the patient is in the course of decreasing the dose of the erythropoiesis-stimulating agent.

(Case where Epoetin is Used as Erythropoiesis-Stimulating Agent and Patient is in Course of Increasing Dose)

The following specifically describes a first coefficient Ka1 and a second coefficient Kb1 in the case where epoetin is used as the erythropoiesis-stimulating agent and the patient is in the course of increasing the dose of epoetin.

In order to determine first coefficient Ka1 and second coefficient Kb1, in consideration of past data of a plurality of patients, a plurality of patients satisfying the following condition are extracted: "the dose of epoetin was constant for three or more months, the dose of the epoetin was increased twice or more in a certain month, and the dose of epoetin was then unchanged for three or more months". From the past data of each of the plurality of extracted patients, the hemoglobin concentration and the dose of epoetin before changing the dose of epoetin, and the hemoglobin concentration and the dose of epoetin three months after changing the dose of epoetin are extracted.

Next, the dose of the erythropoiesis-stimulating agent calculated by substituting various values into the formula (A13) as Ka and Kb, and the actually administered dose of the erythropoiesis-stimulating agent are substituted into the formula (A14), thereby calculating error value A. Then, a combination of Ka value and Kb value for attaining the minimum average value (average error value) of error values A of all the target patients is determined.

Specifically, for example, values from 0 to 9000 in increments of 100 are substituted as Ka, and various values from 0.01 to 500 are substituted as Kb, whereby a Kb value for attaining the minimum average error value is determined for each of the Ka values.

When Ka was in a range from 0 to 5000, a Kb value for attaining the minimum average error value existed for each Ka. On the other hand, when Ka was more than or equal to 5100, Kb for attaining the minimum average error value could not be confirmed. This is presumably due to the following reason: when Ka is more than or equal to 5100, Kb for attaining the minimum average error value is smaller than 0.01. It should be noted that when Ka is in the range from 0 to 5000, the minimum average error value at each Kb was very small to be 0.02 to 0.09.

Figure 6:
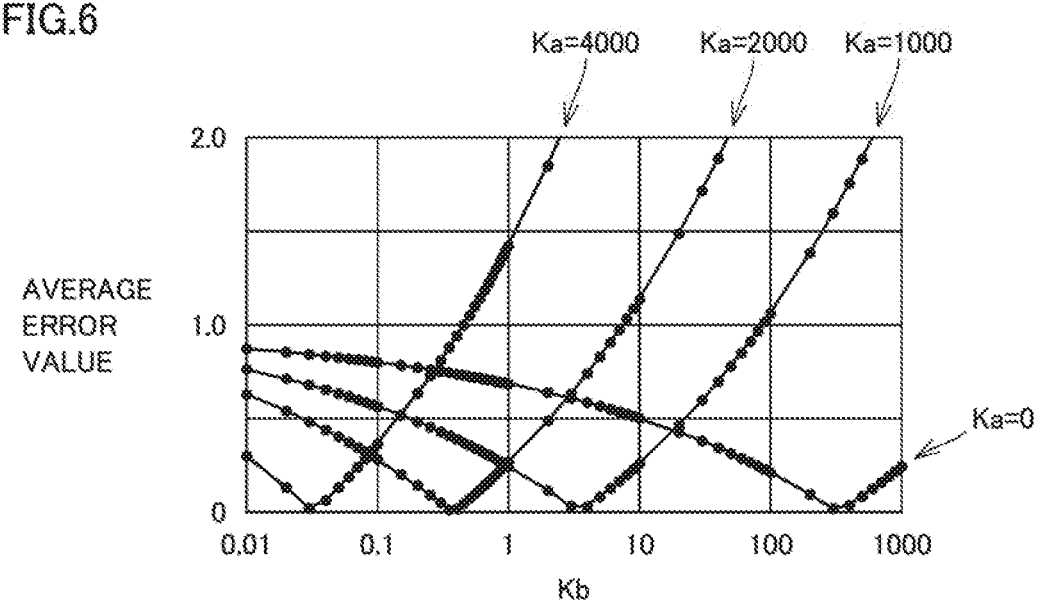
FIG. 6 shows a relation between an average error value and a coefficient Kb in the case where the erythropoiesis-stimulating agent is epoetin and a patient is in a course of increasing the dose of the erythropoiesis-stimulating agent, the average error value being an average error value between the dose of the erythropoiesis-stimulating agent determined based on a predetermined correlation and the actually administered dose of the erythropoiesis-stimulating agent, coefficient Kb being used in the correlation.

FIG. 6 shows a relation between the average error value and second coefficient Kb in the case where the erythropoiesis-stimulating agent is epoetin and the patient is in the course of increasing the dose of the erythropoiesis-stimulating agent, the average error value being an average error value between the dose of the erythropoiesis-stimulating agent determined based on the predetermined correlation and the actually administered dose of the erythropoiesis-stimulating agent, second coefficient Kb being used in the correlation. FIG. 6 illustratively shows the relation between the average error value and Kb in each of cases where Ka is 0, 1000, 2000 and 4000.

As shown in FIG. 6, in each of the cases where Ka is 0, 1000, 2000 and 4000, Kb for attaining the minimum average error value exists.

When a combination of predetermined values of Ka and Kb attains the minimum average error value as described above, the combination of the values of Ka and Kb attains the minimum error between the dose of epoetin calculated by the dose determination program in the present embodiment and the recommended dose of epoetin. Hence, for the combination of Ka and Kb for attaining the minimum average error value, the combination of first coefficient Ka1 and second coefficient Kb1 for calculating the recommended dose of the erythropoiesis-stimulating agent can be employed.

Respective combinations of Ka and Kb for attaining the minimum average error values exist for any values of Ka at least in the range from 0 to 5000. Hence, a combination of Ka and Kb for attaining the minimum average error value, i.e., a combination of first coefficient Ka1 and second coefficient Kb1 is determined by selecting one Ka in the range of from 0 to 5000.

For a plurality of combinations of Ka values and Kb values for attaining the minimum average error value, the Ka values are plotted on the X axis, the respective Kb values corresponding to the Ka values are plotted on the Y axis, and a relational expression between a Ka value and a Kb value for attaining the minimum average error value is determined. That is, a relational expression between first coefficient Ka1 and second coefficient Kb1 is determined.

Figure 7:
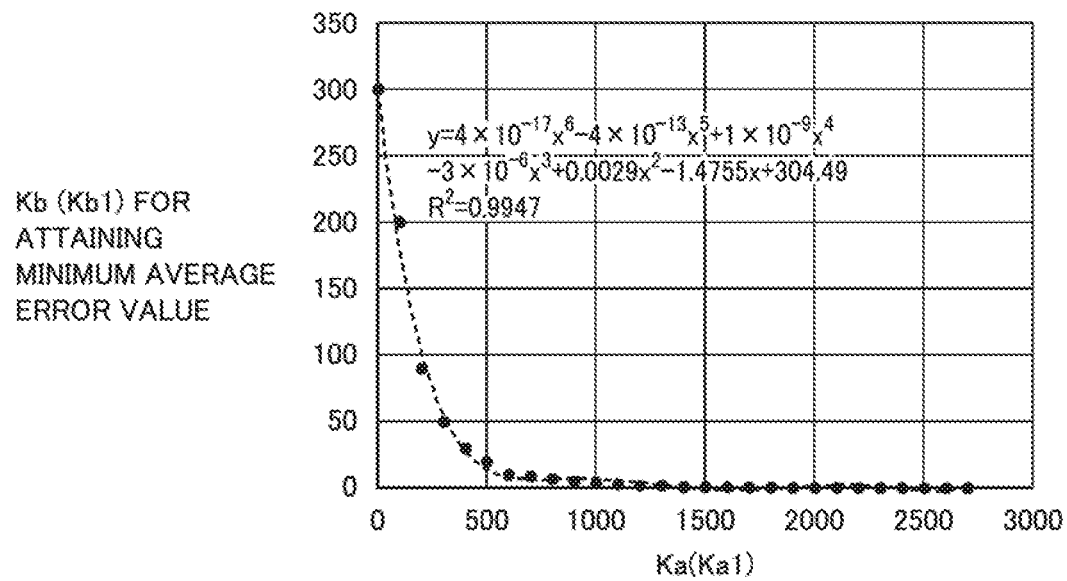
FIG. 7 shows a first example of a relation between a first coefficient Ka1 and a second coefficient Kb1 used for the predetermined correlation in order to attain the minimum average error value as shown in FIG. 6.

FIG. 7 shows a first example of the relation between first coefficient Ka1 and second coefficient Kb1 used for the predetermined correlation in order to attain the minimum average error value as shown in FIG. 6. FIG. 7 shows a case where a plurality of combinations of Ka values and Kb values for attaining the minimum average error value are plotted on the XY coordinates as described above, i.e., shows a case where first coefficients Ka1 and second coefficients Kb1 are plotted on the XY coordinates. As shown in FIG. 7, when Ka1 is larger than 2700, Kb1 has a value close to 0. Hence, a relational expression between a Ka value (Ka1) and a Kb value (Kb1) for attaining the minimum average error value is preferably determined in a range of $0 \le Ka1 \le 2700$.

In the range of $0 \le Ka1 \le 2700$, first coefficient Ka1 and second coefficient Kb1 are recurred to a sixth-degree equation, thus obtaining the following formula (1) as an approximate expression. In this case, a determination coefficient indicating the square of a correlation coefficient is 0.9947.

$$Kb1 = 4 \times 10^{-17} \times Ka1^6 - 4 \times 10^{-13} \times Ka1^5 + 10^{-9} \times Ka1^4 - 3 \times 10^{-6} \times Ka1^3 + 0.0029 \times Ka1^2 - 1.4755 \times Ka1 + 304.49 \quad \text{Formula (1)}$$

As described above, in the case where the erythropoiesis-stimulating agent to be administered is epoetin alfa or epoetin beta, where the unit of the dose of the erythropoiesis-stimulating agent is unit/week and where the patient is in the course of increasing the dose of the erythropoiesis-stimulating agent, when the first coefficient is represented by Ka1, the second coefficient is represented by Kb1, and first coefficient Ka1 falls within the range of $0 \leq Ka1 \leq 2700$, the value of second coefficient Kb1 is calculated based on the above-described formula (1) using first coefficient Ka1.

Figure 8:
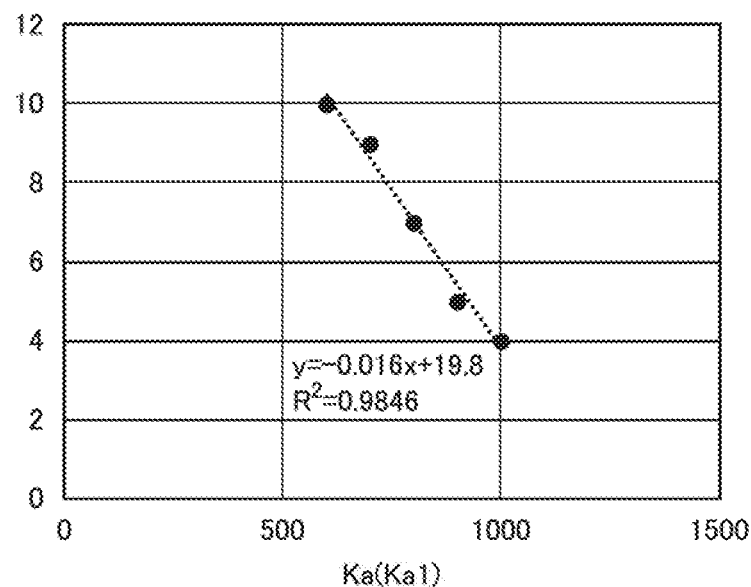
FIG. 8 shows a second example of the relation between first coefficient Ka1 and second coefficient Kb1 used for the predetermined correlation in order to attain the minimum average error value as shown in FIG. 6.

FIG. 8 shows a second example of the relation between first coefficient Ka1 and second coefficient Kb1 used for the predetermined correlation in order to attain the minimum average error value as shown in FIG. 6. In FIG. 8, a plurality of combinations of Ka values and Kb values for attaining the minimum average error value are plotted on the XY coordinates with the range of Ka1 shown in FIG. 7 being narrowed to $600 \leq Ka1 \leq 1000$.

When the range of Ka1 is thus narrowed, first coefficient Ka1 and second coefficient Kb1 are recurred to a first-degree equation, thus obtaining the following formula (5) as an approximate expression. In this case, a determination coefficient indicating the square of a correlation coefficient is 0.9846.

$$Kb1 = -0.016 \times Ka1 + 19.8 \qquad \text{Formula (5)}$$

As described above, in the case where the erythropoiesis-stimulating agent to be administered is epoetin alfa or epoetin beta, where the unit of the dose of the erythropoiesis-stimulating agent is unit/week and where the patient is in the course of increasing the dose of the erythropoiesis-stimulating agent, when the first coefficient is represented by Ka1, the second coefficient is represented by Kb1, and first coefficient Ka1 falls within a range of $600 \leq Ka1 \leq 1000$, the value of second coefficient Kb1 is calculated based on the above-described formula (5) using first coefficient Ka1.

Moreover, when the range of $600 \leq Ka1 \leq 1000$ is narrowed or broadened, or when a range of Ka1 other than $600 \leq Ka1 \leq 1000$ is selected appropriately, second coefficient Kb1 can be represented by a different first-degree equation of first coefficient Ka1 than the above-described formula (5).

By using the formula in which second coefficient Kb1 is represented by the first-degree equation of first coefficient Ka1, the dose can be calculated using the simple formula, whereby a processing speed of the dose determination program can be improved.

(Case where Epoetin is Used as Erythropoiesis-Stimulating Agent and Patient is in Course of Decreasing Dose)

Next, the following specifically describes a first coefficient Ka2 and a second coefficient Kb2 in the case where epoetin is used as the erythropoiesis-stimulating agent and the patient is in the course of decreasing the dose of epoetin.

In order to determine first coefficient Ka2 and second coefficient Kb2, in consideration of past data of a plurality of patients, a plurality of patients satisfying the following condition are extracted: "the dose of epoetin was constant for three or more months, the dose of the epoetin was decreased to ½ or less in a certain month, and the dose of epoetin was then unchanged for three or more months". From the past data of each of the plurality of extracted patients, the hemoglobin concentration and the dose of epoetin before changing the dose of epoetin, and the hemoglobin concentration and the dose of epoetin three months after changing the dose of epoetin are extracted.

Next, the dose of the erythropoiesis-stimulating agent calculated by substituting various values into the formula (A13) as Ka and Kb, and the actually administered dose of the erythropoiesis-stimulating agent are substituted into the formula (A14), thereby calculating error value A. Then, a combination of Ka value and Kb value for attaining the minimum average value (average error value) of error values A of all the target patients is determined.

Specifically, for example, values from 0 to 9000 in increments of 100 are substituted as Ka, and various values from 0.01 to 500 are substituted as Kb, whereby a combination of a Ka value and a Kb value for attaining the minimum average error value is determined for each of them.

When Ka was in a range from 0 to 4800, a Kb value for attaining the minimum average error value existed for each Ka. When Ka was in this range, the minimum average error value was substantially constant at 0.66 to 0.75.

On the other hand, when Ka was more than or equal to 4900 and less than or equal to 9000, Kb for attaining the minimum average error value could not be confirmed. This is presumably due to the following reason: when Ka is more than or equal to 4900 and less than or equal to 9000, Kb for attaining the minimum average error value is smaller than 0.01.

Figure 9:
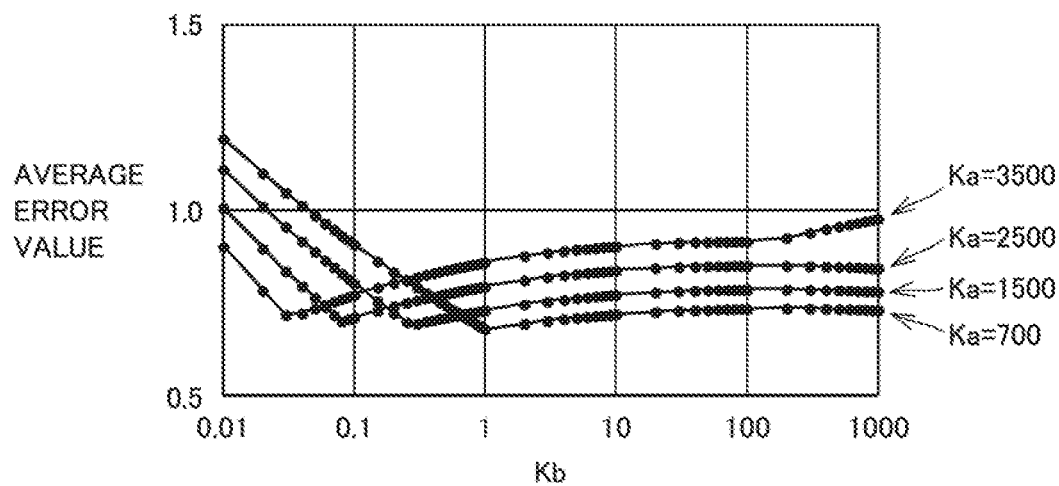
FIG. 9 shows a relation between the average error value and coefficient Kb in the case where the erythropoiesis-stimulating agent is epoetin and the patient is in a course of decreasing the dose of the erythropoiesis-stimulating agent, the average error value being an average error value between the dose of the erythropoiesis-stimulating agent determined based on the predetermined correlation and the actually administered dose of the erythropoiesis-stimulating agent, coefficient Kb being used in the correlation.

FIG. 9 shows a relation between the average error value and second coefficient Kb in the case where the erythropoiesis-stimulating agent is epoetin and the patient is in the course of decreasing the dose of the erythropoiesis-stimulating agent, the average error value being an average error value between the dose of the erythropoiesis-stimulating agent determined based on a predetermined correlation and the actually administered dose of the erythropoiesis-stimulating agent, second coefficient Kb being used in the correlation. FIG. 9 illustratively shows the relation between the average error value and Kb in each of cases where Ka is 700, 1500, 2500, and 3500.

As shown in FIG. 9, in each of the cases where Ka is 700, 1500, 2500, and 3500, Kb for attaining the minimum average error value exists.

When a combination of predetermined values of Ka and Kb attains the minimum average error value as described above, the combination of the values of Ka and Kb attains the minimum error between the dose of epoetin calculated by the dose determination program in the present embodiment and the recommended dose of epoetin. Hence, for the combination of Ka and Kb for attaining the minimum average error value, the combination of first coefficient Ka2 and second coefficient Kb2 for calculating the recommended dose of the erythropoiesis-stimulating agent can be employed.

Respective combinations of Ka and Kb for attaining the minimum average error values exist for any values of Ka at least in the range from 0 to 4800. Hence, a combination of Ka and Kb for attaining the minimum average error value, i.e., a combination of first coefficient Ka2 and second coefficient Kb2 is determined by selecting one Ka in the range of from 0 to 4800.

For a plurality of combinations of Ka values and Kb values for attaining the minimum average error value, the Ka values are plotted on the X axis, the respective Kb values corresponding to the Ka values are plotted on the Y axis, and a relational expression between a Ka value and a Kb value for attaining the minimum average error value is determined. That is, a relational expression between first coefficient Ka2 and second coefficient Kb2 is determined.

Figure 10:
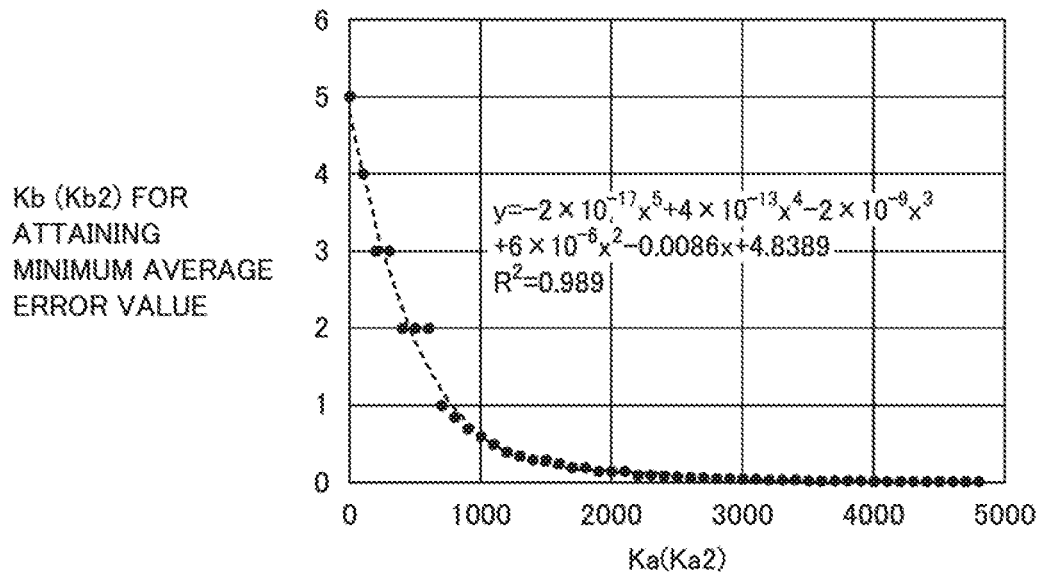
FIG. 10 shows a first example of a relation between a first coefficient Ka2 and a second coefficient Kb2 used for the predetermined correlation in order to attain the minimum average error value as shown in FIG. 9.

FIG. 10 shows a relation between first coefficient Ka2 and first coefficient Kb2 used for the predetermined correlation in order to attain the minimum average error value as shown in FIG. 9. FIG. 10 shows a case where a plurality of combinations of Ka values and Kb values for attaining the minimum average error value are plotted on the XY coordinates as described above, i.e., shows a case where first coefficients Ka2 and second coefficients Kb2 are plotted on the XY coordinates. As shown in FIG. 10, when Ka2 is larger than 4800, Kb2 has a value close to 0. Hence, a relational expression between a Ka value (Ka2) and a Kb value (Kb2) for attaining the minimum average error value is preferably determined in a range of $0 \leq Ka2 \leq 4800$.

In the range of $0 \leq Ka2 \leq 4800$, first coefficient Ka2 and second coefficient Kb2 are recurred to a fifth-degree equation, thus obtaining the following formula (2) as an approximate expression. In this case, a determination coefficient indicating the square of a correlation coefficient is 0.989.

$$Kb2 = -2 \times 10^{-17} \times Ka2^5 + 4 \times 10^{-13} \times Ka2^4 - 2 \times 10^{-9} \times Ka2^3 + 6 \times 10^{-6} \times Ka2^2 - 0.0086 \times Ka2 + 4.8389 \quad \text{Formula (2)}$$

As described above, in the case where the erythropoiesis-stimulating agent to be administered is epoetin alfa or epoetin beta, where the unit of the dose of the erythropoiesis-stimulating agent is unit/week and where the patient is in the course of decreasing the dose of the erythropoiesis-stimulating agent, when the first coefficient is represented by Ka2, the second coefficient is represented by Kb2, and first coefficient Ka2 falls within a range of $0 \leq Ka2 \leq 4800$, the value of second coefficient Kb2 is calculated based on the above-described formula (2) using first coefficient Ka2.

Figure 11:
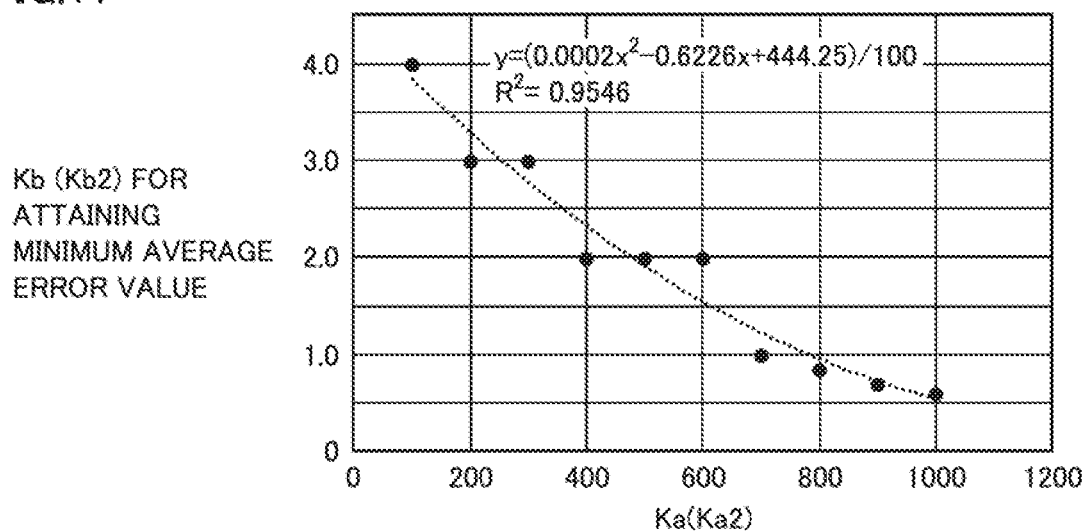
FIG. 11 shows a second example of the relation between first coefficient Ka2 and second coefficient Kb2 used for the predetermined correlation in order to attain the minimum average error value as shown in FIG. 9.

FIG. 11 shows a second example of the relation between first coefficient Ka2 and second coefficient Kb2 used for the predetermined correlation in order to attain the minimum average error value as shown in FIG. 9. In FIG. 11, a plurality of combinations of Ka values and Kb values for attaining the minimum average error value are plotted on the XY coordinates with the range of Ka1 shown in FIG. 9 being narrowed to $100 \leq Ka2 \leq 1000$.

When the range of Ka2 is thus narrowed, first coefficient Ka1 and second coefficient Kb1 are recurred to a second-degree equation, thus obtaining the following formula (6) as an approximate expression. In this case, a determination coefficient indicating the square of a correlation coefficient is 0.9546.

$$Kb2 = (0.0002 \times Ka2^2 - 0.6226 \times Ka2 + 444.25)/100 \quad \text{Formula (6)}$$

As described above, in the case where the erythropoiesis-stimulating agent to be administered is epoetin alfa or epoetin beta, where the unit of the dose of the erythropoiesis-stimulating agent is unit/week and where the patient is in the course of decreasing the dose of the erythropoiesis-stimulating agent, when the first coefficient is represented by Ka2, the second coefficient is represented by Kb2, and first coefficient Ka2 falls within a range of $100 \leq Ka2 \leq 1000$, the value of second coefficient Kb2 is calculated based on the above-described formula (6) using first coefficient Ka2.

Moreover, when the range of $100 \leq Ka2 \leq 1000$ is narrowed or broadened, or when a range of Ka2 other than $100 \leq Ka2 \leq 1000$ is selected appropriately, second coefficient Kb1 can be represented by a different second-degree equation of second coefficient Ka2 than the above-described formula (6).

By using the formula in which second coefficient Kb2 is represented by the second-degree equation of first coefficient Ka2, the dose can be calculated using the simple formula, whereby a processing speed of the dose determination program can be improved.

(Case where Darbepoetin is Used as Erythropoiesis-Stimulating Agent and Patient is in Course of Increasing Dose)

The following specifically describes a first coefficient Ka3 and a second coefficient Kb3 in the case where darbepoetin is used as the erythropoiesis-stimulating agent and the patient is in the course of increasing the dose of darbepoetin.

In order to determine first coefficient Ka3 and second coefficient Kb3, in consideration of past data of a plurality of patients, a plurality of patients satisfying the following condition are extracted: "the dose of darbepoetin was constant for three or more months, the dose of the darbepoetin was increased twice or more in a certain month, and the dose of darbepoetin was then unchanged for three or more months". From the past data of each of the plurality of extracted patients, the hemoglobin concentration and the dose of darbepoetin before changing the dose of darbepoetin, and the hemoglobin concentration and the dose of darbepoetin three months after changing the dose of darbepoetin are extracted.

Next, the dose of the erythropoiesis-stimulating agent calculated by substituting various values into the formula (A13) as Ka and Kb, and the actually administered dose of the erythropoiesis-stimulating agent are substituted into the formula (A14), thereby calculating error value A. Then, a combination of Ka value and Kb value for attaining the minimum average value (average error value) of error values A of all the target patients is determined.

Specifically, for example, values from 0 to 60 in increments of 1 are substituted as Ka, and values from 1 to 15 in increments of 1 are substituted as Kb, whereby a combination of a Ka value and a Kb value for attaining the minimum average error value is determined for each of them.

When Ka was in a range from 0 to 11, a Kb value for attaining the minimum average error value existed for each Ka. On the other hand, when Ka was more than 11, Kb for attaining the minimum average error value could not be confirmed. This is presumably due to the following reason: when Ka is more than 11, Kb for attaining the minimum average error value is smaller than 1. It should be noted that when Ka is in the range from 0 to 11, the minimum average error value for each Kb is very small to be 0.26 to 0.38. As Ka becomes larger, the minimum average error value becomes smaller. Substantially, the minimum average error value is sufficiently small at any Ka value.

Figure 12:
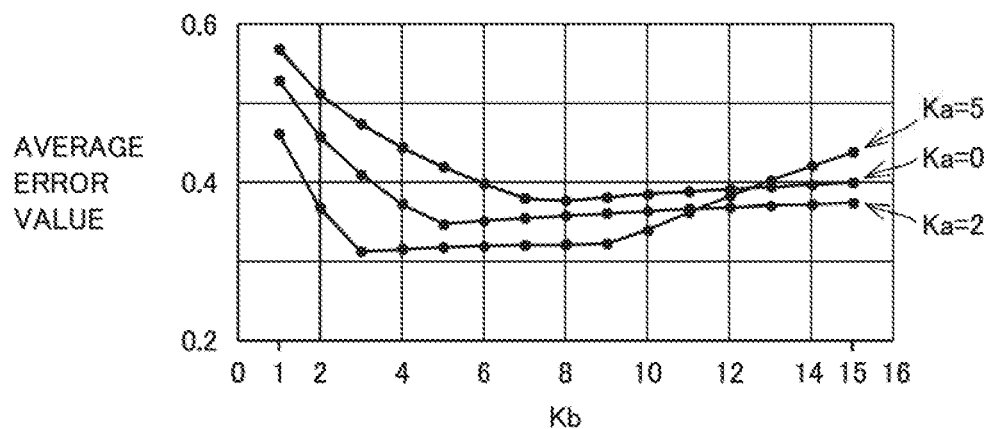
FIG. 12 shows a relation between the average error value and second coefficient Kb in the case where the erythropoiesis-stimulating agent is darbepoetin alfa and the patient is in the course of increasing the dose of the erythropoiesis-stimulating agent, the average error value being an average error value between the dose of the erythropoiesis-stimulating agent determined based on the predetermined correlation and the actually administered dose of the erythropoiesis-stimulating agent, second coefficient Kb being used in the correlation.

FIG. 12 shows a relation between the average error value and second coefficient Kb in the case where the erythropoiesis-stimulating agent is darbepoetin alfa and the patient is in the course of increasing the dose of the erythropoiesis-stimulating agent, the average error value being an average error value between the dose of the erythropoiesis-stimulating agent determined based on the predetermined correlation and the actually administered dose of the erythropoiesis-stimulating agent, second coefficient Kb being used in the correlation. FIG. 12 illustratively shows the relation between the average error value and Kb in each of cases where Ka is 0, 2, and 5.

As shown in FIG. 12, in each of the cases where Ka is 0, 2, and 5, Kb for attaining the minimum average error value exists.

When a combination of predetermined values of Ka and Kb attains the minimum average error value as described above, the combination of the values of Ka and Kb attains the minimum error between the dose of darbepoetin calculated by the dose determination program in the present embodiment and the recommended dose of darbepoetin. Hence, for the combination of Ka and Kb for attaining the minimum average error value, the combination of first coefficient Ka3 and second coefficient Kb3 for calculating the recommended dose of the erythropoiesis-stimulating agent can be employed.

Respective combinations of Ka and Kb for attaining the minimum average error values exist for any values of Ka at least in the range from 0 to 11. Hence, a combination of Ka and Kb for attaining the minimum average error value, i.e., a combination of first coefficient Ka3 and second coefficient Kb3 is determined by selecting one Ka in the range of from 0 to 11.

For a plurality of combinations of Ka values and Kb values for attaining the minimum average error value, the Ka values are plotted on the X axis, the respective Kb values corresponding to the Ka values are plotted on the Y axis, and a relational expression between a Ka value and a Kb value for attaining the minimum average error value is determined. That is, a relational expression between first coefficient Ka3 and second coefficient Kb3 is determined.

Figure 13:
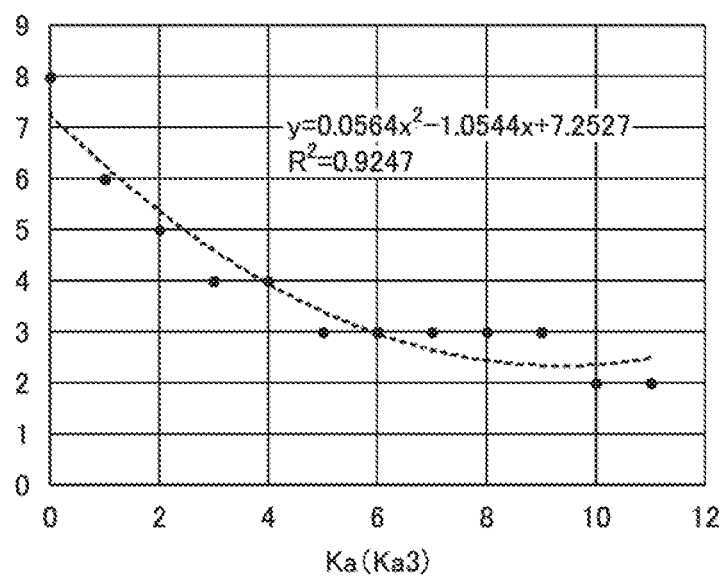
FIG. 13 shows a relation between a first coefficient Ka3 and a second coefficient Kb3 used for the predetermined correlation in order to attain the minimum average error value as shown in FIG. 12.

FIG. 13 shows the relation between first coefficient Ka3 and second coefficient Kb3 used for the predetermined correlation in order to attain the minimum average error value as shown in FIG. 12. FIG. 13 shows a case where a plurality of combinations of Ka values and Kb values for attaining the minimum average error value are plotted on the XY coordinates as described above, i.e., shows a case where first coefficients Ka3 and second coefficients Kb3 are plotted on the XY coordinates. When Ka3 is larger than 11, Kb1 has a value close to 0 as described above. Hence, a relational expression between a Ka value (Ka3) and a Kb value (Kb3) for attaining the minimum average error value is preferably determined in a range of 0≤Ka3≤11.

In the range of 0≤Ka3≤11, first coefficient Ka3 and second coefficient Kb3 are recurred to a second-degree equation, thus obtaining the following formula (3) as an approximate expression. In this case, a determination coefficient indicating the square of a correlation coefficient is 0.9247.

$$Kb3=0.0564 \times Ka3^2-1.0544 \times Ka+7.2527 \quad \text{Formula (3)}$$

As described above, in the case where the erythropoiesis-stimulating agent to be administered is darbepoetin alfa, where the unit of the dose of the erythropoiesis-stimulating agent is μg/week and where the patient is in the course of increasing the dose of the erythropoiesis-stimulating agent, when the first coefficient is represented by Ka3, the second coefficient is represented by Kb3, and first coefficient Ka3 falls within a range of 0≤Ka3≤11, the value of second coefficient Kb3 is calculated based on the above-described formula (3) using first coefficient Ka3.

(Case where Darbepoetin is Used as Erythropoiesis-Stimulating Agent and Patient is in Course of Decreasing Dose)

The following specifically describes a first coefficient Ka4 and a second coefficient Kb4 in the case where darbepoetin is used as the erythropoiesis-stimulating agent and the patient is in the course of decreasing the dose of darbepoetin.

In order to determine first coefficient Ka4 and second coefficient Kb4, in consideration of past data of a plurality of patients, a plurality of patients satisfying the following condition are extracted: "the dose of darbepoetin was constant for three or more months, the dose of the darbepoetin was decreased to ½ or less in a certain month, and the dose of darbepoetin was then unchanged for three or more months". From the past data of each of the plurality of extracted patients, the hemoglobin concentration and the dose of darbepoetin before changing the dose of darbepoetin, and the hemoglobin concentration and the dose of darbepoetin three months after changing the dose of darbepoetin are extracted.

Next, the dose of the erythropoiesis-stimulating agent calculated by substituting various values into the formula (A13) as Ka and Kb, and the actually administered dose of the erythropoiesis-stimulating agent are substituted into the formula (A14), thereby calculating error value A. Then, a combination of Ka value and Kb value for attaining the minimum average value (average error value) of error values A of all the target patients is determined.

Specifically, for example, values from 0 to 60 in increments of 1 are substituted as Ka, and various values from 1 to 100000000 are substituted as Kb, whereby a combination of a Ka value and a Kb value for attaining the minimum average error value is determined for each of them.

When Ka was in a range from 41 to 60, a Kb value for attaining the minimum average error value existed for each Ka. On the other hand, when Ka is less than or equal to 40, Kb for attaining the minimum average error value could not be confirmed. This is presumably due to the following reason: when Ka is less than or equal to 40, Kb for attaining the minimum average error value is larger than 100000000. It should be noted that when Ka is in the range from 41 to 60, the respective minimum average error values for Kb were substantially constant to be 1.53 to 1.84. That is, substantially, the minimum average error value is the same at any Ka value.

Figure 14:
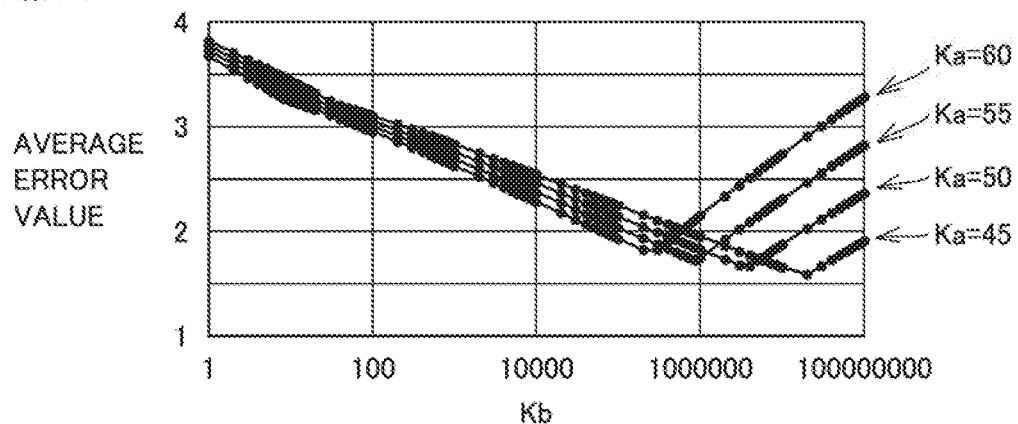
FIG. 14 shows a relation between the average error value and coefficient Kb in the case where the erythropoiesis-stimulating agent is darbepoetin alfa and the patient is in the course of decreasing the dose of the erythropoiesis-stimulating agent, the average error value being an average error value between the dose of the erythropoiesis-stimulating agent determined based on the predetermined correlation and the actually administered dose of the erythropoiesis-stimulating agent, coefficient Kb being used in the correlation.

FIG. 14 shows a relation between the average error value and second coefficient Kb in the case where the erythropoiesis-stimulating agent is darbepoetin alfa and the patient is in the course of decreasing the dose of the erythropoiesis-stimulating agent, the average error value being an average error value between the dose of the erythropoiesis-stimulating agent determined based on the predetermined correlation and the actually administered dose of the erythropoiesis-stimulating agent, second coefficient Kb being used in the correlation. FIG. 14 illustratively shows the relation between the average error value and Kb in each of cases where Ka is 45, 50, 55, and 60.

As shown in FIG. 14, in each of the cases where Ka is 45, 50, 55, and 60, Kb for attaining the minimum average error value exists.

When a combination of predetermined values of Ka and Kb attains the minimum average error value as described above, the combination of the values of Ka and Kb attains the minimum error between the dose of darbepoetin calculated by the dose determination program in the present embodiment and the recommended dose of darbepoetin. Hence, for the combination of Ka and Kb for attaining the minimum average error value, the combination of first coefficient Ka4 and second coefficient Kb4 for calculating the recommended dose of the erythropoiesis-stimulating agent can be employed.

Respective combinations of Ka and Kb for attaining the minimum average error values exist for any values of Ka at least in the range from 41 to 60. Hence, a combination of Ka and Kb for attaining the minimum average error value, i.e., a combination of first coefficient Ka4 and second coefficient Kb4 is determined by selecting one Ka in the range of from 41 to 60.

For a plurality of combinations of Ka values and Kb values for attaining the minimum average error value, the Ka values are plotted on the X axis, the respective Kb values corresponding to the Ka values are plotted on the Y axis, and a relational expression between a Ka value and a Kb value for attaining the minimum average error value is determined. That is, a relational expression between first coefficient Ka4 and second coefficient Kb4 is determined.

Figure 15:
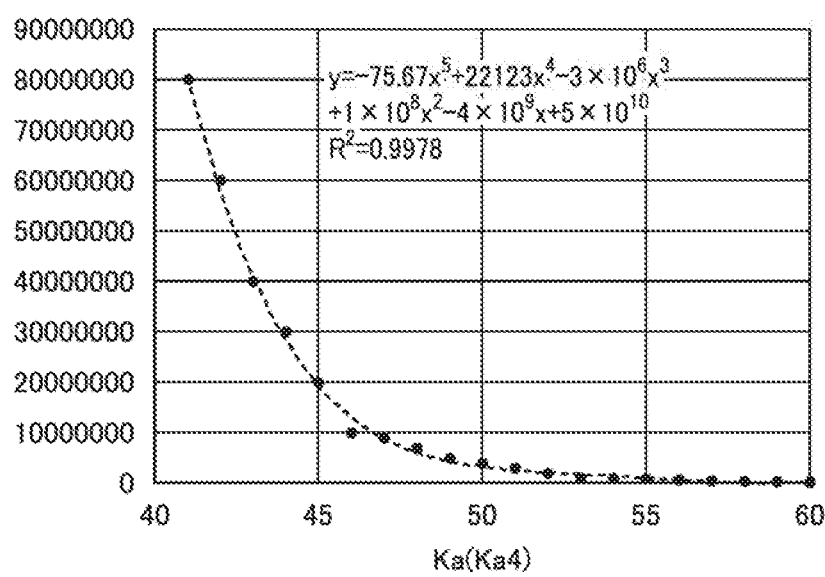
FIG. 15 shows a first example of a relation between a first coefficient Ka4 and a second coefficient Kb4 used for the predetermined correlation in order to attain the minimum average error value as shown in FIG. 14.

FIG. 15 shows the relation between first coefficient Ka4 and second coefficient Kb4 used for the predetermined correlation in order to attain the minimum average error value as shown in FIG. 14. FIG. 15 shows a case where a plurality of combinations of Ka values and Kb values for attaining the minimum average error value are plotted on the XY coordinates as described above, i.e., shows a case where first coefficients Ka4 and second coefficients Kb4 are plotted on the XY coordinates. When Ka4 is less than or equal to 40, Kb4 has a value close to 100000000 as described above. Hence, a relational expression between a Ka value and a Kb value for attaining the minimum average error value is preferably determined in a range of $41 \leq Ka4 \leq 60$.

In the range of $41 \leq Ka4 \leq 60$, first coefficient Ka4 and second coefficient Kb4 are recurred to a fifth-degree equation, thus obtaining the following formula (4) as an approximate expression. In this case, a determination coefficient indicating the square of a correlation coefficient is 0.9978.

$$Kb4 = -75.67 \times Ka4^5 + 22123 \times Ka4^4 - 3 \times 10^6 \times Ka4^3 + 10^8 \times Ka4^2 - 4 \times 10^9 \times Ka4 + 5 \times 10^{10} \quad \text{Formula (4)}$$

As described above, in the case where the erythropoiesis-stimulating agent to be administered is darbepoetin alfa, where the unit of the dose of the erythropoiesis-stimulating agent is μg/week and where the patient is in the course of decreasing the dose of the erythropoiesis-stimulating agent, when the first coefficient is represented by Ka4, the second coefficient is represented by Kb4, and first coefficient Ka4 falls within a range of $41 \leq Ka4 \leq 60$, the value of second coefficient Kb4 is calculated based on the above-described formula (4) using first coefficient Ka4.

Figure 16:
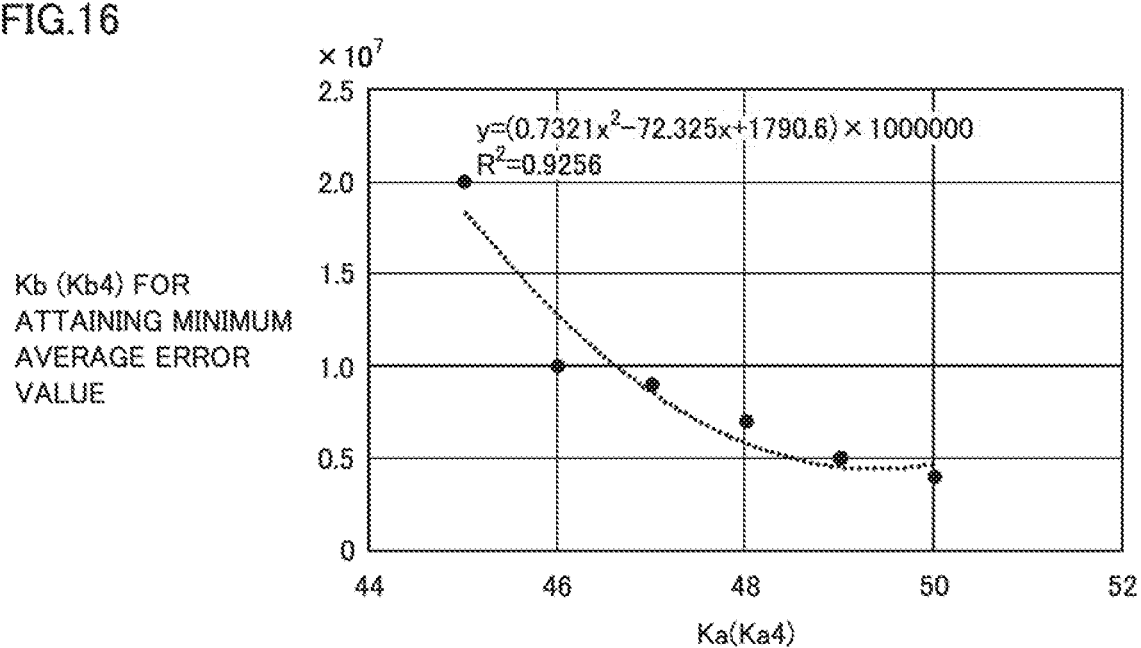
FIG. 16 shows a second example of the relation between first coefficient Ka4 and second coefficient Kb4 used for the predetermined correlation in order to attain the minimum average error value as shown in FIG. 14.

FIG. 16 shows a second example of the relation between first coefficient Ka4 and second coefficient Kb4 used for the predetermined correlation in order to attain the minimum average error value as shown in FIG. 14. In FIG. 16, a plurality of combinations of Ka values and Kb values for attaining the minimum average error value are plotted on the XY coordinates with the range of Ka4 shown in FIG. 15 being narrowed to $45 \leq Ka4 \leq 50$.

When the range of Ka4 is thus narrowed, first coefficient Ka4 and second coefficient Kb4 are recurred to a second-degree equation, thus obtaining the following formula (7) as an approximate expression. In this case, a determination coefficient indicating the square of a correlation coefficient is 0.9256.

$$Kb4 = (0.7321 \times Ka4^2 - 72.325 \times Ka4 + 1790.6) \times 1000000 \quad \text{Formula (7)}$$

As described above, in the case where the erythropoiesis-stimulating agent to be administered is darbepoetin alfa, where the unit of the dose of the erythropoiesis-stimulating agent is μg/week and where the patient is in the course of decreasing the dose of the erythropoiesis-stimulating agent, when the first coefficient is represented by Ka4, the second coefficient is represented by Kb4, and first coefficient Ka4 falls within a range of $45 \leq Ka4 \leq 50$, the value of second coefficient Kb4 is calculated based on the above-described formula (7) using first coefficient Ka4.

Moreover, when the range of $45 \leq Ka4 \leq 50$ is narrowed or broadened, or when a range of Ka4 other than $45 \leq Ka4 \leq 50$ is selected appropriately, second coefficient Kb4 can be represented by a different second-degree equation of first coefficient Ka4 than the above-described formula (7).

By using the formula in which second coefficient Kb4 is represented by the second-degree equation of first coefficient Ka4, the dose can be calculated using the simple formula, whereby a processing speed of the dose determination program can be improved.

Figure 17:
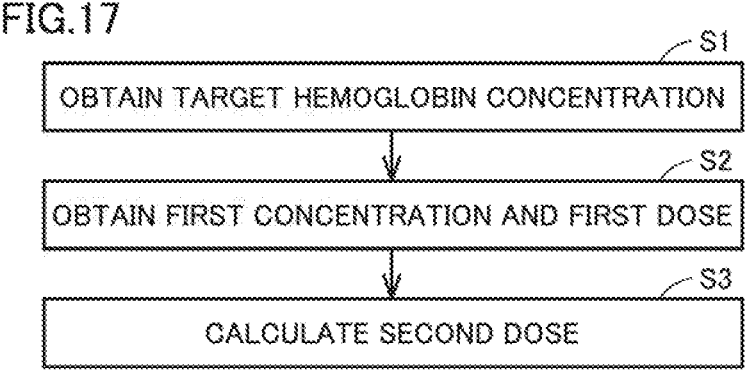
FIG. 17 shows a flowchart showing a process of administering the erythropoiesis-stimulating agent according to the embodiment.

FIG. 17 shows a flowchart showing a process of administering the erythropoiesis-stimulating agent according to the embodiment. With reference to FIG. 17, the following describes the process of administering the erythropoiesis-stimulating agent according to the embodiment.

As shown in FIG. 17, in a process of determining the dose of the erythropoiesis-stimulating agent, in a step S1, controller 110 obtains a target hemoglobin concentration to be reached by a patient.

Controller 110 may obtain the target hemoglobin concentration from a value input from input device 180. When the target hemoglobin concentration is input in advance and is stored in a storage location such as storage device 140, ROM 120, or RAM 130, controller 110 may obtain the target hemoglobin concentration by reading out the target hemoglobin concentration from the storage location.

In a step S2, controller 110 obtains a first concentration and a first dose in a first stable state in which a hemoglobin concentration is stable at the first concentration by repeatedly administering the first dose a plurality of times.

Controller 110 may obtain the first concentration and the first dose from values input from input device 180. When the first concentration and the first dose are input in advance and are stored in a storage location such as storage device 140, ROM 120, or RAM 130, controller 110 may obtain the first concentration and the first dose by reading out the first concentration and the first dose from the storage location.

It should be noted that in the embodiment, it is illustrated that step 2 is performed after step 1; however, it is not limited to this. Step 2 may be performed before step 1 or may be performed simultaneously with step 1.

In a step S3, based on the obtained target hemoglobin concentration, the obtained first concentration and the obtained first dose, controller 110 calculates a second dose of the erythropoiesis-stimulating agent to be administered by a fixed amount in order to reach the target hemoglobin concentration.

On this occasion, controller 110 calculates the second dose using a predetermined correlation between the second dose and each of the first concentration, the first dose, and the target hemoglobin concentration. The correlation is stored in a storage location such as storage device 140, ROM 120, or RAM 130 in advance.

The correlation is calculated based on a first relational expression between the first concentration and the first dose in the first stable state, and a second relational expression between the target hemoglobin concentration and the second dose in the state in which the hemoglobin concentration is stable at the target hemoglobin concentration.

In the first relational expression, as described in the formula (A11), the logarithmic value of the value obtained by multiplying, by the second coefficient, the value obtained by adding the first coefficient to the first dose, and the first concentration in the first stable state are proportional to each other.

In the second relational expression, as described in the formula (A12), the logarithmic value of the value obtained by multiplying, by the first coefficient, the value obtained by adding the first coefficient to the second dose, and the target hemoglobin concentration in the state (second stable state) in which the hemoglobin concentration is stable at the target hemoglobin concentration are proportional to each other.

Here, in the case where the erythropoiesis-stimulating agent to be administered is epoetin alfa or epoetin beta, where the unit of the dose of the erythropoiesis-stimulating agent is unit/week and where the patient is in the course of increasing the dose of the erythropoiesis-stimulating agent, when the first coefficient is represented by Ka1, the second coefficient is represented by Kb1, and first coefficient Ka1 falls within a range of $0 \leq Ka1 \leq 2700$, the value of second coefficient Kb1 is a value calculated based on the above-described formula (1). Moreover, when the range of first coefficient Ka1 is 600≤Ka1≤1000, the value of second coefficient Kb1 is a value calculated from the above-described formula (5).

Here, in the case where the erythropoiesis-stimulating agent to be administered is epoetin alfa or epoetin beta, where the unit of the dose of the erythropoiesis-stimulating agent is unit/week and where the patient is in the course of decreasing the dose of the erythropoiesis-stimulating agent, when the first coefficient is represented by Ka2, the second coefficient is represented by Kb2, and first coefficient Ka2 falls within a range of 0≤Ka2≤4800, the value of second coefficient Kb2 is a value calculated based on the above-described formula (2). Moreover, when the range of first coefficient Ka2 is 100≤Ka2≤1000, the value of second coefficient Kb2 is a value calculated from the above-described formula (6).

In the case where the erythropoiesis-stimulating agent to be administered is darbepoetin alfa, where the unit of the dose of the erythropoiesis-stimulating agent is μg/week and where the patient is in the course of increasing the dose of the erythropoiesis-stimulating agent, when the first coefficient is represented by Ka3, the second coefficient is represented by Kb3, and first coefficient Ka3 falls within a range of 0≤Ka3≤11, the value of second coefficient Kb3 is calculated based on the above-described formula (3).

In the case where the erythropoiesis-stimulating agent to be administered is darbepoetin alfa, where the unit of the dose of the erythropoiesis-stimulating agent is μg/week and where the patient is in the course of decreasing the dose of the erythropoiesis-stimulating agent, when the first coefficient is represented by Ka4, the second coefficient is represented by Kb4, and first coefficient Ka4 falls within a range of 41≤Ka4≤60, the value of second coefficient Kb4 is calculated based on the above-described formula (4). Moreover, when the range of first coefficient Ka4 is 45≤Ka4≤50, the value of second coefficient Kb4 is a value calculated from the above-described formula (7).

Controller 110 substitutes the determined first coefficient Ka and second coefficient Kb into the above-described formula (A13), substitutes the target hemoglobin concentration, first concentration, and first dose obtained in step S1 and step S2 into the formula (A13), and uses the formula (A13) to calculate the dose (second dose) of the erythropoiesis-stimulating agent to be administered by the fixed amount in order to reach the target hemoglobin concentration.

It should be noted that even when any one of epoetin alfa, epoetin beta, and darbepoetin alfa is used as the erythropoiesis-stimulating agent, controller 110 may obtain first coefficient Ka and second coefficient Kb by way of values input from input device 180.

Moreover, controller 110 may obtain first coefficient Ka and second coefficient Kb in the following manner: only first coefficient Ka is input from input device 180, and second coefficient Kb is calculated using the input first coefficient Ka and the formula (1) to formula (7) stored in advance in the storage location such as storage device 140, ROM 120, or RAM 130.

Moreover, controller 110 may obtain first coefficient Ka and second coefficient Kb by reading out first coefficient Ka and second coefficient Kb stored in advance in the storage location such as storage device 140, ROM 120, or RAM 130.

As described above, in the present embodiment, the second dose can be calculated using the simple algorithm by causing a computer to perform the steps of: obtaining a predetermined target hemoglobin concentration; obtaining a first concentration and a first dose in a first stable state in which a hemoglobin concentration is stable at the first concentration by repeatedly administering the first dose a plurality of times; and calculating a second dose of the erythropoiesis-stimulating agent based on the obtained target hemoglobin concentration, the obtained first concentration, and the obtained first dose, the second dose of the erythropoiesis-stimulating agent being to be administered by a fixed amount. Moreover, by administering the second dose by the fixed amount, the blood hemoglobin concentration is stably maintained at the target value, and a range of fluctuation thereof can be reduced.

EXAMPLE

For each of a plurality of patients for each whom a dose of erythropoiesis-stimulating agent had been adjusted by a dialysis-specialized doctor based on his/her experience so as to allow a hemoglobin concentration to fall within a range of more than or equal to 10.0 g/dL and less than or equal to 11.0 g/dL, the dose was determined from the third month using the dose determination program according to the present embodiment, and the erythropoiesis-stimulating agent was administered based on the determined dose.

Epoetin and darbepoetin were used as the erythropoiesis-stimulating agent. In each case, the following matters were examined: a change of the hemoglobin concentration with respect to an administration period; a change of an amount of deviation in which the hemoglobin concentration was deviated from the target hemoglobin concentration; and a change of the dose. It should be noted that epoetin was administered to 35 patients, and darbepoetin was administered to 70 patients. Moreover, the target hemoglobin concentration was set to 10.5 g/dL.

Figure 18A:
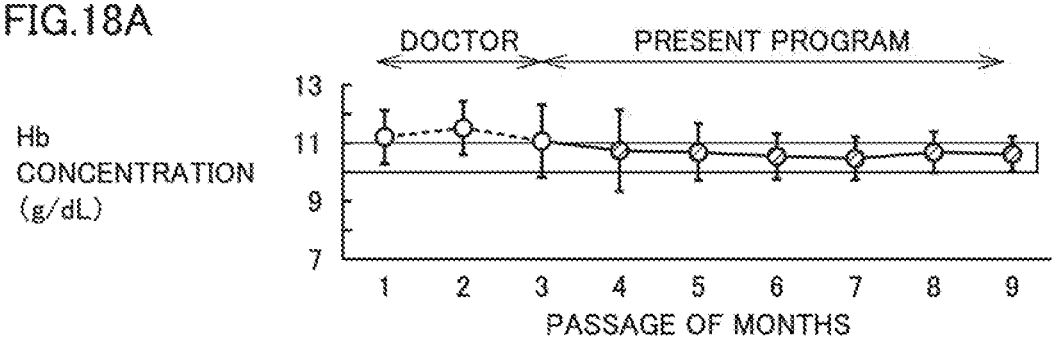
FIG. 18A shows a change of the hemoglobin concentration in the case where epoetin was used as the erythropoiesis-stimulating agent and the dose of the erythropoiesis-stimulating agent calculated by the dose determination program in the embodiment was administered after a specialized doctor had administered the erythropoiesis-stimulating agent based on his/her experience.

FIG. 18A shows the change of the hemoglobin concentration in the case where epoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

As shown in FIG. 18A, the average value of the hemoglobin concentration, which had been more than or equal to 11 g/dL during a period in which the dialysis-specialized doctor had administered epoetin based on his/her experience, was decreased toward the target value after starting to use the dose determination program according to the present embodiment. With three months after using the dose determination program, the average value of the hemoglobin concentration reached substantially the center of the target range. Thereafter, the average value of the hemoglobin concentration was also changed within the target range.

Figure 18B:
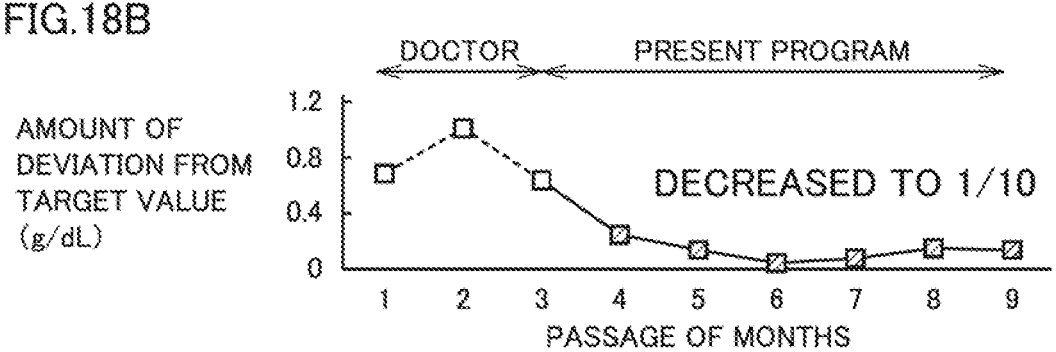
FIG. 18B shows a change of an amount of deviation of the hemoglobin concentration from a target hemoglobin concentration in the case where epoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

FIG. 18B shows the change of the amount of deviation of the hemoglobin concentration from the target hemoglobin concentration in the case where epoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

As shown in FIG. 18B, the amount of deviation of the hemoglobin concentration from the target hemoglobin concentration was decreased after starting to use the dose determination program according to the present embodiment. The amount of deviation after three months since the use of the dose determination program was less than or equal to ⅒ of the amount of deviation during the period in which the dialysis-specialized doctor had administered epoetin based on his/her experience.

Here, the amount of deviation means a degree of achievement of the target hemoglobin concentration. The result shown in FIG. 18B indicates that the degree of achievement of the target hemoglobin concentration was increased by using the dose determination program according to the present embodiment.

Figure 18C:
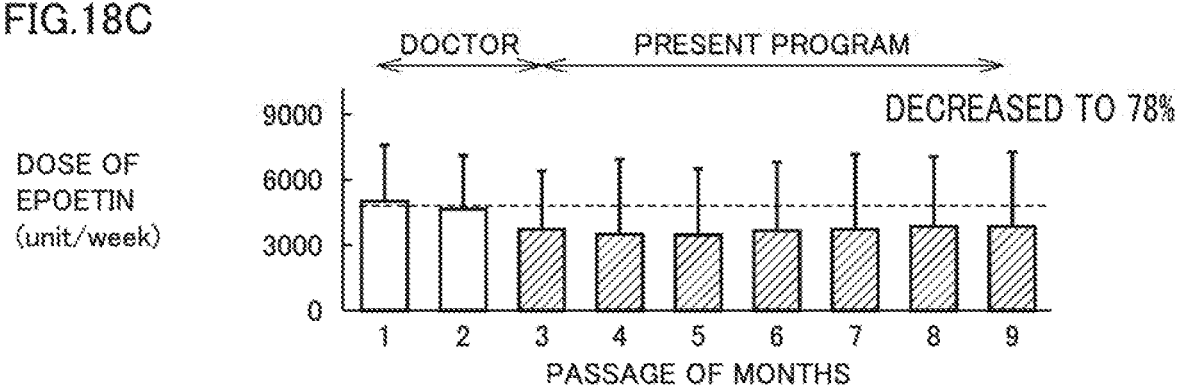
FIG. 18C shows a change of the dose in the case where epoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

FIG. 18C shows the change of the dose in the case where epoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

As shown in FIG. 18C, the dose of epoetin had been already decreased when the dose was first calculated using the dose determination program according to the present embodiment, and the average dose of epoetin throughout the period of use of the dose determination program was substantially 78% of the average dose of epoetin during the period in which the dialysis-specialized doctor had administered based on his/her experience.

Figure 19A:
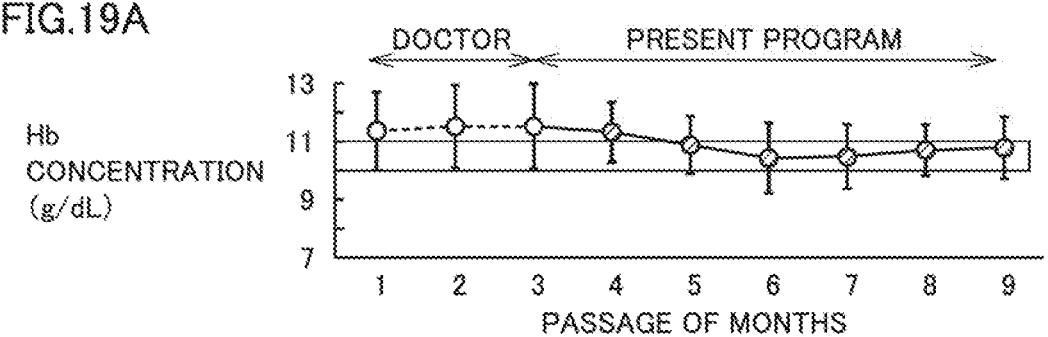
FIG. 19A shows a change of the hemoglobin concentration in the case where darbepoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

FIG. 19A shows the change of the hemoglobin concentration in the case where darbepoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

As shown in FIG. 19A, the average value of the hemoglobin concentration, which had been more than or equal to 11 g/dL during the period in which the dialysis-specialized doctor had administered darbepoetin based on his/her experience, was decreased toward the target value after starting to use the dose determination program according to the present embodiment. With three months after using the dose determination program, the average value of the hemoglobin concentration reached substantially the center of the target range. Thereafter, the average value of the hemoglobin concentration was also changed within the target range.

Figure 19B:
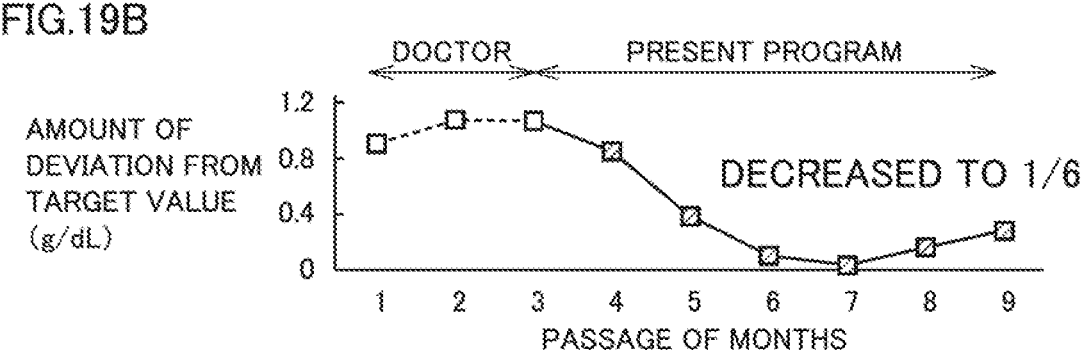
FIG. 19B shows a change of an amount of deviation of the hemoglobin concentration from the target hemoglobin concentration in the case where darbepoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

FIG. 19B shows the change of the amount of deviation of the hemoglobin concentration from the target hemoglobin concentration in the case where darbepoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

As shown in FIG. 19B, the amount of deviation of the hemoglobin concentration from the target hemoglobin concentration was decreased after starting to use the dose determination program according to the present embodiment. The amount of deviation after three months since the use of the dose determination program was less than or equal to ⅙ of the amount of deviation during the period in which the dialysis-specialized doctor had administered epoetin based on his/her experience.

Here, the amount of deviation means a degree of achievement of the target hemoglobin concentration. The result shown in FIG. 19B indicates that the degree of achievement of the target hemoglobin concentration was increased by using the dose determination program according to the present embodiment.

Figure 19C:
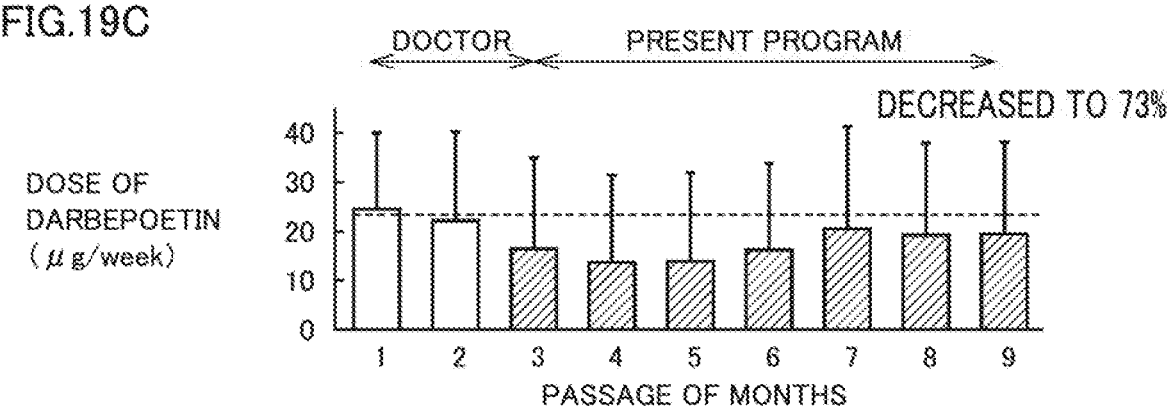
FIG. 19C shows a change of the dose in the case where darbepoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

FIG. 19C shows the change of the dose in the case where darbepoetin was used as the erythropoiesis-stimulating agent and the dose of the erythropoiesis-stimulating agent calculated by the dose determination program in the embodiment was administered after the specialized doctor had administered the erythropoiesis-stimulating agent based on his/her experience.

As shown in FIG. 19C, the dose of darbepoetin had been already decreased when the dose was first calculated using the dose determination program according to the present embodiment, and the average dose of darbepoetin throughout the period of use of the dose determination program was substantially 73% of the average dose of darbepoetin during the period in which the dialysis-specialized doctor had administered based on his/her experience.

From the above results, it can be said that it was confirmed experimentally that by using dose determination program 141 according to the present embodiment and administering the dose calculated by the program, the hemoglobin concentration in blood can be stably maintained at a target value and the range of fluctuation of the hemoglobin concentration in blood can be made small.

Moreover, a dialysis-specialized doctor tends to control the hemoglobin concentration to be slightly higher for the sake of a precaution against the hemoglobin concentration becoming lower than the target value; however, in the dose determination program according to the present embodiment, it can be said that such an apprehension is unnecessary. Accordingly, a burden on the doctor can be also reduced.

The embodiments disclosed herein are illustrative and non-restrictive in any respect. The scope of the present invention is defined by the terms of the claims, and includes any modifications within the scope and meaning equivalent to the terms of the claims.

REFERENCE SIGNS LIST

100: dose determination device; 101: first obtaining unit; 102: second obtaining unit; 103: calculation unit; 110: controller; 120: ROM; 130: RAM; 140: storage device; 141: dose determination program; 150: display interface; 160: input interface; 170: display unit; 180: input device; 200: hardware.

The invention claimed is:

1. A dose determination device that determines a dose of an erythropoiesis-stimulating agent, the dose determination device comprising:
   a computer comprising a CPU, ROM, and RAM, the computer programmed to:
   obtain a predetermined target hemoglobin concentration;
   obtain a first hemoglobin concentration and a first dose of erythropoiesis-stimulating agent in a stable state in which a hemoglobin concentration is stable at the first hemoglobin concentration when repeatedly administering the first dose a plurality of times over a first time period of three or more months; and
   calculate a second constant dose of the erythropoiesis-stimulating agent based on the obtained target hemoglobin concentration, the obtained first hemoglobin concentration, and the obtained first dose, the second constant dose of the erythropoiesis-stimulating agent configured to be administered by a fixed amount,
   wherein the computer is programmed to calculate the second constant dose using a predetermined correlation between the second constant dose and each of the first hemoglobin concentration, the first dose, and the target hemoglobin concentration, wherein the computer is programmed to calculate the correlation based on a first relational expression between the first hemoglobin concentration and the first dose in the stable state and a second relational expression between the target hemoglobin concentration and the second constant dose in a state in which the hemoglobin concentration is stable at the target hemoglobin concentration when repeatedly administering the second constant dose over a second time period of three or more months.

2. The dose determination device according to claim 1, wherein
in the first relational expression, a logarithmic value of a value obtained by multiplying, by a second coefficient, a value obtained by adding a first coefficient to the first dose, and the first hemoglobin concentration in the stable state are proportional to each other, and
in the second relational expression, a logarithmic value of a value obtained by multiplying, by the second coefficient, a value obtained by adding the first coefficient to the second constant dose, and the target hemoglobin concentration in the state in which the hemoglobin concentration is stable at the target hemoglobin concentration are proportional to each other.

3. The dose determination device according to claim 2, wherein the first coefficient and the second coefficient differ depending on a case where a patient is in a course of increasing a dose of the erythropoiesis-stimulating agent and a case where the patient is in a course of decreasing the dose of the erythropoiesis-stimulating agent.

4. The dose determination device according to claim 2, wherein in a case where the erythropoiesis-stimulating agent to be administered is epoetin alfa or epoetin beta, where a unit of a dose of the erythropoiesis-stimulating agent is unit/week and where a patient is in a course of increasing the dose of the erythropoiesis-stimulating agent, when the first coefficient is represented by Ka1, the second coefficient is represented by Kb1, and the first coefficient Ka1 falls within a range of $0 \leq Ka1 \leq 2700$, a value of the second coefficient Kb1 is calculated based on the following formula (1) using the first coefficient Ka1:

$$Kb1=(4\times10^{-17}\times Ka1^6)-(4\times10^{-13}\times Ka1^5)+(10^{-9}\times Ka1^4)-(3\times10^{-6}\times Ka1^3)+(0.0029\times Ka1^2)-(1.4755\times Ka1)+304.49 \qquad \text{Formula (1)}.$$

5. The dose determination device according to claim 2, wherein in a case where the erythropoiesis-stimulating agent to be administered is epoetin alfa or epoetin beta, where a unit of a dose of the erythropoiesis-stimulating agent is unit/week and where a patient is in a course of decreasing the dose of the erythropoiesis-stimulating agent, when the first coefficient is represented by Ka2, the second coefficient is represented by Kb2, and the first coefficient Ka2 falls within a range of $0 \leq Ka2 \leq 4800$, a value of the second coefficient Kb2 is calculated based on the following formula (2) using the first coefficient Ka2:

$$Kb2=(-2\times10^{-17}\times Ka2^5)+(4\times10^{-13}\times Ka2^4)-(2\times10^{-9}\times Ka2^3)+(6\times10^{-6}\times Ka2^2)-(0.0086\times Ka2)+4.8389 \qquad \text{Formula (2)}.$$

6. The dose determination device according to claim 2, wherein in a case where the erythropoiesis-stimulating agent to be administered is darbepoetin alfa, where a unit of a dose of the erythropoiesis-stimulating agent is μg/week and where a patient is in a course of increasing the dose of the erythropoiesis-stimulating agent, when the first coefficient is represented by Ka3, the second coefficient is represented by Kb3, and the first coefficient Ka3 falls within a range of $0 \leq Ka3 \leq 11$, a value of the second coefficient Kb3 is calculated based on the following formula (3) using the first coefficient Ka3:

$$Kb3=(0.0564\times Ka3^2)-(1.0544\times Ka3)+7.2527 \qquad \text{Formula (3)}.$$

7. The dose determination device according to claim 2, wherein in a case where the erythropoiesis-stimulating agent to be administered is darbepoetin alfa, where a unit of a dose of the erythropoiesis-stimulating agent is μg/week and where a patient is in a course of decreasing the dose of the erythropoiesis-stimulating agent, when the first coefficient is represented by Ka4, the second coefficient is represented by Kb4, and the first coefficient Ka4 falls within a range of $41 \leq Ka4 \leq 60$, a value of the second coefficient Kb4 is calculated based on the following formula (4) using the first coefficient Ka4:

$$Kb4=(-75.67\times Ka4^5)+(22123\times Ka4^4)-(3\times10^6\times Ka4^3)+(10^8\times Ka4^2)-(4\times10^9\times Ka4)+5\times10^{10} \qquad \text{Formula (4)}.$$

8. The dose determination device according to claim 2, wherein the second coefficient is represented by a first-degree equation of the first coefficient.

9. The dose determination device according to claim 8, wherein in a case where the erythropoiesis-stimulating agent to be administered is epoetin alfa or epoetin beta, where a unit of a dose of the erythropoiesis-stimulating agent is unit/week and where a patient is in a course of increasing the dose of the erythropoiesis-stimulating agent, when the first coefficient is represented by Ka1, the second coefficient is represented by Kb1, and the first coefficient Ka1 falls within a range of $600 \leq Ka1 \leq 1000$, a value of the second coefficient Kb1 is calculated based on the following formula (5) using the first coefficient Ka1:

$$Kb1=(-0.016\times Ka1)+19.8 \qquad \text{Formula (5)}.$$

10. The dose determination device according to claim 2, wherein the second coefficient is represented by a second-degree equation of the first coefficient.

11. The dose determination device according to claim 10, wherein in a case where the erythropoiesis-stimulating agent to be administered is epoetin alfa or epoetin beta, where a unit of a dose of the erythropoiesis-stimulating agent is unit/week and where a patient is in a course of decreasing the dose of the erythropoiesis-stimulating agent, when the first coefficient is represented by Ka2, the second coefficient is represented by Kb2, and the first coefficient Ka2 falls within a range of $100 \leq Ka2 \leq 1000$, a value of the second coefficient Kb2 is calculated based on the following formula (6) using the first coefficient Ka2:

$$Kb2=((0.0002\times Ka2^2)-(0.6226\times Ka2)+444.25)/100 \qquad \text{Formula (6)}.$$

12. The dose determination device according to claim 10, wherein in a case where the erythropoiesis-stimulating agent to be administered is darbepoetin alfa, where a unit of a dose of the erythropoiesis-stimulating agent is μg/week and where a patient is in a course of decreasing the dose of the erythropoiesis-stimulating agent, when the first coefficient is represented by Ka4, the second coefficient is represented by Kb4, and the first coefficient Ka4 falls within a range of $45 \leq Ka4 \leq 50$, a value of the second coefficient Kb4 is calculated based on the following formula (7) using the first coefficient Ka4:

$$Kb4=((0.7321\times Ka4^2)-(72.325\times Ka4)+1790.6)\times 1000000 \qquad \text{Formula (7)}.$$

* * * * *